(12) United States Patent
Messersmith et al.

(10) Patent No.: US 9,637,597 B2
(45) Date of Patent: May 2, 2017

(54) DOPA-MELANIN FORMATION IN HIGH IONIC STRENGTH SOLUTIONS

(71) Applicant: Northwestern University, Evanston, IL (US)

(72) Inventors: Phillip B. Messersmith, Clarendon Hills, IL (US); Jinghao Kuang, Evanston, IL (US)

(73) Assignee: Northwestern University, Evanston, IL (US)

( * ) Notice: Subject to any disclaimer, the term of this patent is extended or adjusted under 35 U.S.C. 154(b) by 33 days.

(21) Appl. No.: 14/666,905

(22) Filed: Mar. 24, 2015

(65) Prior Publication Data

US 2015/0274892 A1    Oct. 1, 2015

Related U.S. Application Data

(60) Provisional application No. 61/969,920, filed on Mar. 25, 2014.

(51) Int. Cl.
| | | |
|---|---|---|
| *A61F 13/00* | (2006.01) | |
| *C08G 73/06* | (2006.01) | |
| *C09D 179/04* | (2006.01) | |
| *A61L 31/16* | (2006.01) | |
| *A61L 31/10* | (2006.01) | |
| *C02F 1/28* | (2006.01) | |
| *C08G 61/12* | (2006.01) | |
| *A61K 9/16* | (2006.01) | |
| *C02F 101/20* | (2006.01) | |
| *A61K 9/00* | (2006.01) | |

(52) U.S. Cl.
CPC ........ *C08G 73/0672* (2013.01); *A61K 9/1641* (2013.01); *A61L 31/10* (2013.01); *A61L 31/16* (2013.01); *C02F 1/285* (2013.01); *C08G 61/124* (2013.01); *C09D 179/04* (2013.01); *A61K 9/0024* (2013.01); *A61L 2300/23* (2013.01); *A61L 2300/404* (2013.01); *A61L 2420/06* (2013.01); *C02F 2101/20* (2013.01); *Y10T 428/265* (2015.01)

(58) Field of Classification Search
None
See application file for complete search history.

(56) References Cited

U.S. PATENT DOCUMENTS

| | | | |
|---|---|---|---|
| 2008/0149566 A1* | 6/2008 | Messersmith | C09D 5/1662 210/702 |
| 2013/0209969 A1 | 8/2013 | Wang et al. | |
| 2014/0206630 A1* | 7/2014 | Messersmith | C08J 7/065 514/25 |

FOREIGN PATENT DOCUMENTS

JP    H11196895 A    7/1999

OTHER PUBLICATIONS

Bettinger, et al., Biocompatibility of Biodegradable Semiconducting Melanin Films for Nerve Tissue Engineering, Biomaterials, 2009, 30:3050-3057.
De Albuquerque, et al., Determination of Thermal and Optical Parameters of Melanins by Photopyroelectric Spectroscopy, Applied Physics Letters, 2005, 87:061920-1-061920-3.
Deziderio, et al., Thin Films of Synthetic Melanin, Journal of Non-Crystalline Solids, 2004, 338-340:634-638.
Lebedev, et al., Paramagnetic Calcium Melanins, Biophysics, 2013, 58(1):37-42.
Sono, et al., Melanin-Based Coatings as Lead-Binding Agents, Bioinorganic Chemistry and Applications, vol. 2012, Article ID 361803, 10 pages.
Tamura, et al., A Reagent and a Method for Specifically Measuring an Insect Body Fluid Reactive Substance, 1999, Chemical Abstracts Service, Retrieved by European Patent Office as International Searching Authority From STN Database Accession No. 1999:462747.
PCT International Search Report and Written Opinion, PCT/US2015/022243, Jun. 9, 2015, 14 pages.

* cited by examiner

*Primary Examiner* — Susan Tran
(74) *Attorney, Agent, or Firm* — Quarles & Brady, LLP

(57) ABSTRACT

Methods of synthesizing a DOPA-melanin (DM) polymer are disclosed, as well as compositions comprising the DM polymer and uses thereof. The method comprises contacting a reactant such as 3,4-dihydroxyphenylalanine (DOPA) with a high concentration aqueous salt solution under oxidative conditions. The resulting DM polymer may form as insoluble particles or as a coating on a substrate surface. Exemplary uses for the DM polymers include removing heavy metal ions from contaminated solutions or capturing and delivering cationic drugs such as gentamicin.

31 Claims, 27 Drawing Sheets

DOPA-MELANIN FORMATION IN HIGH IONIC STRENGTH SOLUTIONS

CROSS-REFERENCE TO RELATED APPLICATIONS

This application claims priority to U.S. Provisional Appn. No. 61/969,920 filed Mar. 25, 2014, the entirety of which is incorporated by reference in this document for all purposes.

STATEMENT REGARDING FEDERALLY-SPONSORED RESEARCH OR DEVELOPMENT

This invention was made with government support under grant number R37 DE014193 awarded by the National Institutes of Health. The government has certain rights to the invention.

FIELD OF INVENTION

This invention generally relates to polymeric particles and coatings. More particularly, this invention relates to DOPA-melanin polymers that spontaneously form in solutions of high ionic strength as surface coatings or insoluble particles.

BACKGROUND OF THE INVENTION

Melanins are widespread in nature, providing pigmentation, photoprotection, anti-oxidant, metal binding and other biological properties. An important subclass of melanins is eumelanin, which forms from tyrosine through a pathway involving 3,4-dihydroxyphenylalanine (DOPA) oxidation, intramolecular cyclization, oligomerization, and aggregation to form an insoluble and heterogeneous solid. Research on eumelanins is in part motivated by an interest in understanding structure-property relationships in the context of biological function, but also due to a growing interest in the interesting optical, electrical properties and technological applications of melanin thin films.

Synthetic and natural melanins are insoluble in many solvents and this property represents a challenge for processing into useful forms such as thin films. In the past, the deposition of melanin-like thin films on substrates has been accomplished by solution casting, (electro)spraying, spin coating, electrochemical deposition, and pulsed laser deposition. In addition to generally requiring the solubilization of melanin in organic solvent or aqueous NaOH or ammonia, most reported methods are either line-of-sight, require sophisticated equipment, employ complex multi-step protocols, or can only be performed on conducting substrates. Due to these limitations, there remains a significant need for simple and versatile approaches to melanin thin film deposition. Methods for forming melanin thin films that avoid the need for significant infrastructure and that can accommodate a variety of substrate compositions, shapes and configurations, will accelerate the development of practical applications for this interesting class of bioinspired materials.

A simple and versatile method to modify surfaces with melanin-like coatings involving dip-coating of substrates into an aqueous solution of catecholamine mimics of DOPA-rich mussel adhesive proteins, such as dopamine, is disclosed in U.S. Patent Publication No. 2008/0149566 (which is incorporated by reference in this document for all purposes). Dopamine undergoes spontaneous auto-oxidation in mildly basic and aerated aqueous solution to form an adherent polydopamine (PDA) film on virtually any substrate. PDA, also referred to as dopamine-melanin because of its chemical similarity to eumelanin, can then act as a primer for further modification leading to numerous applications such as biomolecule immobilization, surface energy modification, biomineralization and biosensing. Molecules of interest can also be co-deposited simultaneously with dopamine in a one-step reaction to create surfaces with desired properties.

Several derivatives of dopamine and other catecholamines polymerize in a similar fashion onto a wide variety of substrates. For example, norepinephrine was shown to polymerize into adherent films with the added ability of initiating ring-opening polymerization of $\epsilon$-caprolactone due to the presence of a hydroxyl group not found on dopamine. It would be of interest to spontaneously polymerize DOPA-melanin (DM) films on a variety of substrates in a similar fashion as PDA, as this would further accelerate technological applications of eumelanin-like thin films. In comparison to PDA, DM films would be expected to exhibit a higher concentration of free carboxylic acids that can be exploited for a variety of applications.

However, historical reports of the alkaline auto-oxidation of DOPA in water or low ionic strength buffer resulted in a melanin-like product which is soluble or a solution-stable supramolecular nanoaggregate. Those in the art have experienced difficulty forming adherent films from DOPA using the standard conditions developed for spontaneous PDA film formation (buffered aerated $H_2O$, pH 8-9). In-situ grown DM films have only been shown to achieve thicknesses of 10 nm or less under conditions that typically yield much thicker films using dopamine. Thus, compared to PDA, DM films are considerably more difficult to grow on substrates by spontaneous autoxidation of DOPA.

Accordingly, there is a need in the art for improved methods of producing DM films and particles for a variety of applications.

SUMMARY OF THE INVENTION

We disclose herein the spontaneous in-situ autooxidative deposition of DM films in a facile manner at high ionic strength. Thick adherent DM films formed on a wide variety of substrates, including metal oxide, noble metal and polymer. DM films possess many of the desirable characteristics of PDA films but with some advantages, namely higher hydrophilicity and the ability to electrostatically bind and release cations. The latter property was exploited for fabricating antibacterial coatings by loading and release of a cationic aminoglycoside from DM films.

We further disclose herein that high ionic strength alkaline buffer solutions can be used to autooxidize DOPA without requiring a surface substrate, resulting in the formation of insoluble particles of DOPA-melanin (DM) having a high 5,6-dihydroxyindole carboxylic acid (DHIC) content. Such particles have high binding capacities for metal ions, with the extent of bonding related to the salt type and concentration included in the solution. Thus, the resulting DM particles can be used for, among other things, heavy metal remediation.

Accordingly, in a first aspect, the invention encompasses a method of synthesizing a DOPA-melanin (DM) polymer. The method includes the step of contacting a reactant having the following formula with a high concentration aqueous salt solution under oxidative conditions:

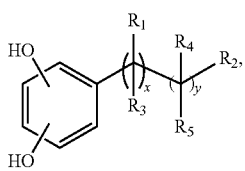

wherein each of $R_1$, $R_3$, $R_4$, and $R_5$ is independently selected from the group consisting of a $C_{1-3}$ alkyl, a primary amine, a secondary amine, a halide, a hydrogen, a hydroxyl, a carboxylic acid, an aldehyde, a carboxylic ester or a carboxamide; wherein at least one of $R_1$, $R_3$, $R_4$, and $R_5$ is a primary or secondary amine; wherein x ranges from 0 to 3 and wherein y ranges from 0 to 3, provided that x or y is at least 1; and wherein $R_2$ is a carboxylic acid. As a result of performing the method, a DOPA-melanin (DM) polymer is formed.

In some embodiments, x and y are each 1, $R_2$ is —COOH, and $R_5$ is —$NH_2$. In some such embodiments, the reactant is 3,4-dihydroxyphenylalanine (DOPA).

In some embodiments, the concentration of salt in the aqueous salt solution is greater than 100 mM. Optionally, the concentration of salt greater than 200 mM, or greater than 500 mM.

In some non-limiting exemplary embodiments, the salt used is a sodium salt, a potassium salt, a magnesium salt, or a calcium salt. In some embodiments, the aqueous salt solution is an alkaline solution.

In some embodiments, the method further includes the step of contacting the reactant and the high concentration aqueous salt solution with a surface. As a result of performing this step, a DM coating or film forms on the surface.

In some such embodiments, the DM coating forms on the surface spontaneously. In other such embodiments, the DM coating is greater than 10 nm in thickness. In yet other such embodiments, the surface includes a negatively charged substrate.

In some embodiments, the DM polymer formed is in the form of insoluble particles.

In a second aspect, the invention encompasses the DOPA-melanin (DM) polymer that is formed by performing the method described above.

In some embodiments, the DM polymer includes residual carboxylic acid moieties.

In some embodiments, the DM polymer is in the form of a coating on a substrate surface. In some such embodiments, the coating is greater than 10 nm in thickness. In other such embodiments, the substrate surface is the surface of a medical device.

In some embodiments, the DM polymer further includes a heavy metal ion or a cationic drug captured on the polymer. In some such embodiments, the cationic drug is a cationic aminoglycoside.

In some embodiments, the DM polymer is in the form of insoluble particles.

In a third aspect, the invention encompasses a method of reducing the number of metal ions in a fluid. The method includes the steps of contacting the DOPA-melanin (DM) polymer described above with a fluid comprising one or more metal ions. As a result, the DM polymer binds to at least one of the metal ions, thereby reducing the number of metal ions in the fluid. In some embodiments, the one or more metal ions may be $Pb^{2+}$, $Cd^{2+}$, $Cu^{2+}$, or $Hg^{2+}$.

In a fourth aspect, the invention encompasses a method of delivering a cationic drug. The method includes the steps of (a) contacting the DOPA-melanin (DM) polymer as described above with one or more cationic drugs, whereby the cationic drug is reversibly bound to the DM polymer; and (b) releasing the cationic drug from the DM polymer.

In some embodiments, the cationic drug is a cationic aminoglycoside. Exemplary aminoglycosides that may be used include without limitation gentamicin, kanamycin, amikacin, tobramycin, dibekasin, arbekacin, sisomicin, netilmicin, neomycin, and streptomycin.

In a fifth aspect, the invention encompasses a kit for synthesizing a DOPA-melanin (DM) polymer. Such a kit includes: a) a reactant having the following formula:

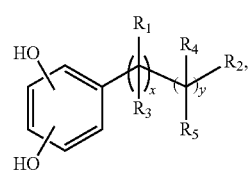

wherein each of $R_1$, $R_3$, $R_4$, and $R_5$ is independently selected from the group consisting of a $C_{1-3}$ alkyl, a primary amine, a secondary amine, a halide, a hydrogen, a hydroxyl, a carboxylic acid, an aldehyde, a carboxylic ester or a carboxamide; wherein at least one of $R_1$, $R_3$, $R_4$, and $R_5$ is a primary or secondary amine; wherein x ranges from 0 to 3 and wherein y ranges from 0 to 3, provided that x or y is at least 1; and wherein $R_2$ is a carboxylic acid; wherein x ranges from 0 to 10 and wherein y ranges from 0 to 10, provided that x or y is at least 1; b) a metal salt; and c) instructions for use.

In some embodiments, the metal salt may be a sodium salt, a potassium salt, a magnesium salt, or a calcium salt. In some embodiments, the kit may further include an alkaline buffer.

In some embodiments, the kit may further include a substrate surface to be coated with the DM polymer. In some such embodiments, the substrate surface is the surface of a medical device.

In the specification and in the claims, the terms "including" and "comprising" are open-ended terms and should be interpreted to mean "including, but not limited to . . . ." These terms encompass the more restrictive terms "consisting essentially of" and "consisting of."

DETAILED DESCRIPTION OF THE INVENTION

I. In General

Figure 1:
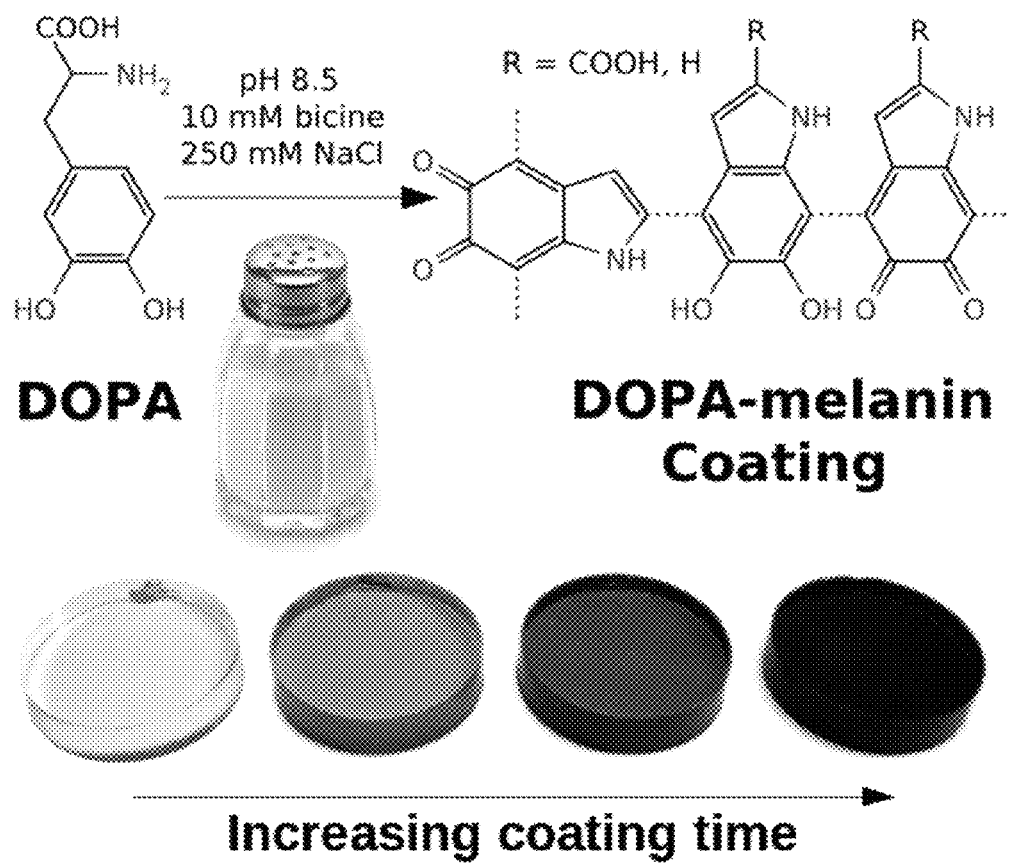
FIG. 1 is a schematic diagram illustrating conformal DOPA-melanin film formation by simple dip-coating in an alkaline DOPA solution at high ionic strength.

The present invention provides a novel method of spontaneously producing a DOPA-melanin polymer in the form of a deposited film or coating on a surface or in the form of an insoluble particle. The present invention's interfacial and synthetic chemistry will be useful in important fields including biocompatible coatings of medical devices, surface modifications of drug delivery carriers and tissue engineering scaffolds, biosensors, biofouling-resistant, industrial and consumer coatings, semiconductors, metal removal, surface catalysts and next generation electronic displays. Certain non-limiting embodiments of the invention are described in more detail below.

II. Reactants for Spontaneous Autooxidation

The reactant used in the spontaneous autoxidation process disclosed herein reacts under oxidizing conditions in a high ion strength, and preferably alkaline, solution, to make the DOPA-melanin (DM) polymer. The reactant has the following formula:

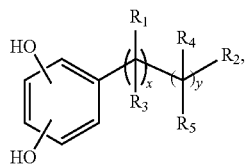

wherein each of $R_1$, $R_3$, $R_4$, and $R_5$ is independently selected from the group consisting of a $C_{1-3}$ alkyl, a primary amine, a secondary amine, a halide, a hydrogen, a hydroxyl, a carboxylic acid, an aldehyde, a carboxylic ester or a carboxamide; wherein at least one of $R_1$, $R_3$, $R_4$, and $R_5$ is a primary or secondary amine; wherein x ranges from 0 to 3 and wherein y ranges from 0 to 3, provided that x or y is at least 1; and wherein $R_2$ is a carboxylic acid.
DOPA.

In one such embodiment, the reactant is 3,4-dihydroxyphenylalanine (DOPA) or salts thereof:

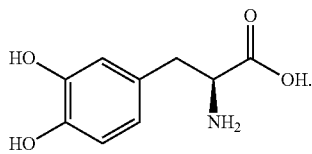 [SMILES: N[C@@H](Cc1ccc(O)c(O)c1)C(=O)O]

III. High Ionic Strength Solution for Spontaneous Autooxidation

The high ionic strength salt solution used in the present invention can also include additives such as fillers, pigments, wetting agents, viscosity modifiers, stabilizers, antioxidants or cross-linking agents. The reactant can be cross-linked if desired. If desired, the salt solution can include various adjuvants such as small particle fillers, surface active agents, UV absorbers, photo-initiators, colorants and indicators.

By "high ionic strength," we mean that the concentration of salt in the solution used is above 100 mM, with other embodiments using a solution having a salt concentration of above 200 mM, above 300 mM, above 400 mM, or above 500 mM. Salt concentration ranges that can be used include 100-5000 mM, 100-4000 mM, 100-3000 mM, 100-2000 mM, 100-1000 mM, 100-500 mM, 100-400 mM, 100-300 mM, 150-5000 mM, 150-4000 mM, 150-3000 mM, 150-2000 mM, 150-1000 mM, 150-500 mM, 150-400 mM, 150-300 mM, 200-5000 mM, 200-4000 mM, 200-3000 mM, 200-2000 mM, 200-1000 mM, 200-500 mM, 200-400 mM, and 200-300 mM.

By "alkaline," we mean that the pH value of the solution ranges from 7.1 to 12, with a preferred pH ranging from 7.5 to 10, with a further preferred pH ranging from 7.5 to 8.5. An alkaline solution triggers polymerization of reactant onto the substrate surface.

By "solution," we mean a mixture wherein at least one solute is dissolved in a solvent that contains water, but that also includes miscible solutions of water and organic solvents such as acetone, chloroform, dichloromethane, methanol, ethanol, isopropanol, dimethylformamide, dimethylsulfoxide and hexane. Preferably, the solution is made just prior to use, although the solution may be stored for at least brief periods of time before use.

By "under oxidative conditions," we mean alkaline pH of aqueous solutions and non-aqueous solvents with dissolved oxygen or organic bases such as triethylamine. In alternative embodiments, solutions comprising oxidants such as hydrogen peroxide, sodium periodate, tertiary butylhydroperoxide, organic peroxides, quinones including benzoquinones, napthoquinones, anthraquinones, nitroaryl compounds, metal oxidants including $Cu^{2+}$, $Fe^{3+}$, $Co^{3+}$ and $Mn^{3+}$, phenols, indoles, aminobenzenes and more can be used to initiate polymerization via oxidization of the reactant.

In one embodiment, a substrate is immersed or dipped in the reactant solution. The examples below illustrate preferred contacting methods. However, a variety of techniques can be employed to contact the substrate surface with the reactant solution including, without limitation, swabbing, dip coating, spin coating, die coating, ink jet coating, spraying, screen printing (e.g., rotary screen printing), gravure printing, photolithographic printing and flexographic printing, microcontact printing, nanolithography.

On contact, a DM film forms on the substrate surface. In a preferred embodiment, the DM film comprises a smooth, continuous polymeric coating on the substrate surface, the polymeric coating having a substantially constant thickness. As a general guide, the polymeric coating exists on the substrate surface in a thickness of greater than 10 nm. In some embodiments, the thickness ranges from about 11 to 1000 nm, preferably ranging from about 11 to 100 nm.

In some embodiments, the synthesis is spontaneous. By "spontaneous," we mean that the reaction is thermodynamically favored, and thus proceeds without a continuous input of work or force. As the skilled artisan would recognize, a non-limiting example of a non-spontaneous reaction is electrolysis, which requires an externally applied electrical current.

IV. Substrates

In some embodiments, the method comprises contacting at least a portion of the substrate with the reactant, as described above.

By "substrate," we mean any inorganic or organic substrate. For instance, the substrate can be an organic solid, an inorganic solid, or a combination of organic and inorganic solids that provides a surface for receiving the adherent polymer. Suitable organic or inorganic substrates may also be fibrous, filamentous, meshes, porous or solvent-swollen (e.g. hydrogel or organogel) objects. Preferably, care is taken when selecting the substrate so that there will be an adequate degree of adhesion between the substrate and the reactant.

Suitable inorganic substrates include but are not limited to inorganic substrates such as quartz, glass, silica and other oxides or ceramics such as alumina, indium tin oxide, lithium tantalate ($LiTaO_3$), lithium niobate ($LiNbO_3$), gallium arsenide (GaAs), silicon carbide (SiC), langasite (LGS), zinc oxide (ZnO), aluminum nitride (AlN), aluminum oxide ($Al_2O_3$), silicon (Si), silicon nitride ($Si_3N_4$), and lead zirconium titanate ("PZT"), titanium oxide ($TiO_2$), niobium oxide ($Nb_2O_5$); and metals or alloys such as aluminum, copper, gold, silver and steel. Other suitable inorganic substrates include, without limitation, mica, diamond and nickel titanium (NiTi).

Suitable organic substrates include but are not limited to organic substrates such as thermoplastics including polyesters (e.g., polyethylene terephthalate or polyethylene naphthalates), polyacrylates (e.g., polymethyl methacrylate or "PMMA"), poly(vinyl acetate) ("PVAC"), poly(vinylbutyral) ("PVB"), poly(ethyl acrylate) ("PEA"), poly(diphenoxyphosphazene) ("PDPP"), polycarbonate ("PC"), polypropylene ("PP"), high density polyethylene ("HDPE"), low density polyethylene ("LDPE"), polysulfone ("PS"), polyether sulfone ("PES"), polyurethane ("PUR"), polyamide ("PA"), poly(dimethylsiloxane) ("PDMS"), polyvinyl chloride ("PVC"), polyvinylidene fluoride ("PVdF"), polystyrene ("PSy") and polyethylene sulfide; and thermoset plastics such as cellulose derivatives, polyimide, polyimide benzoxazole and polybenzoxazole. Other suitable organic substrates include, without limitation, graphite, carbon nanotubes, fullerenes, graphene, poly(glycolic acid), poly (lactic acid), and poly(lactic-co-glycolic acid) and Teflon®.

Untreated Substrates.

The method of the present invention can be used on substrates in any condition. For instance, substrates having existing coatings such as paint, oil, grease, protectants and the like can be used without any additional pre-treatments or cleaning.

Pre-Treated Substrates.

In another embodiment, the substrate can instead or in addition to be pretreated to enhance film formation. Preferred pretreatments include but are not limited to electron and ion beam irradiation, electrical discharge in the presence of a suitable reactive or non-reactive atmosphere (e.g., plasma, glow discharge, corona discharge, dielectric barrier discharge or atmospheric pressure discharge); chemical pretreatment (e.g., with a low solids solution of polyvinylidene dichloride or with a solvent-borne mixture of a polyester resin and an aziridine cross-linker); flame pretreatment; ultraviolet light pretreatment with or without ozone pretreatment; and incorporating functional polymers into the substrate when a polymeric substrate is employed. In an alternative embodiment, the present invention provides a method of enhancing coatings on artificially or naturally damaged/altered substrates.

V. Uses

Current applications for reactant-treated substrates are many and include, without limitation, applications for anti-biofouling and anti-oxidant surfaces; medical devices for catheters, stents, artificial bones, teeth, and dialysis tubes; semiconductors for bio-MEMS, and sensors; and metal nanoparticles and quantum dots for sensors, diagnostics, and cellular imaging.

Antibacterial and Antifouling Surfaces.

In this embodiment, a substrate surface coated with the DM polymer may exhibit anti-microbial properties, or may include a bound antibiotic possessing such properties. See Example 1 below for a non-limiting example.

Reactant-treated substrates can be used to provide biofouling-resistant substrate for use in medical and dental devices and implants, watercraft hulls, off-shore and on-shore structures of manmade or natural composition, water treatment facilities, liquid handling or movement structures such as pipelines and chemical treatment facilities, food processing surfaces, and construction and housing materials. By "biofouling" we mean the nonspecific adsorptions of macromolecules, cells, proteins, bacteria, algae and other organisms and their byproducts at solid-liquid or solid-air interfaces, often resulting in adverse effects on performance, safety, and longevity of, for instance, medical devices and sensors. By "resistant" we mean substrates modified so as to prevent the nonspecific adsorptions of macromolecules, cells, proteins, bacteria, algae and other organisms and their byproducts at solid-liquid or solid-air interfaces associated with biofouling. Currently, surface immobilization of polyethylene glycol (PEG or PEGylation) has been the most popular approach for non-fouling surface preparation, but anchoring PEG molecules in a surface independent manner remains a major challenge.

Preventing Oxidation.

In this embodiment, the DM polymer may exhibit anti-oxidant properties, or may protect the surface underneath from oxidation.

Drug Delivery.

The DM polymer may reversibly bind to certain cationic drugs. Thus, it can be used in drug delivery. See Example 1 below for a non-limiting example.

Electroless Metallization.

In this embodiment, one would preferably treat a surface with a reactant in a high ionic strength solution as described above, and then expose the treated surface to metal solutions to form an adherent metal film.

Nucleophile Addition.

In this embodiment, one would preferably contact a substrate with a reactant in a high ionic strength solution as described above, and then expose the reactant-treated substrate to a nucleophile. By "nucleophile" we mean an electron-rich species with a tendency to be attracted to the nuclear charge of an electron-poor species, the electrophile. Important nucleophiles include primary and secondary amines, thiols, azides, nitriles, aldehydes, imidazoles, azides, polyhexamethylene dithiocarbonate, hydrogen, hydroxyls, carboxylic acids, aldehydes, carboxylic esters or carboxamides, etc.

TABLE 1

A partial list of important nucleophiles

| Cl$^-$ | Br$^-$ | I$^-$ | |
| | HO$^-$ | *R—OH | *RO$^-$ |
| H$_2$S | HS$^-$ | *R—SH | *R—S$^-$ |
| —NH$_2$ | N$_3^-$ | $^-$C≡N | *R—C≡C$^-$ |

*R can be anything.

Suitable nucleophiles may comprise parts of more complex molecules, such as proteins or nucleic acids.

Polymer Grafting.

In this embodiment, one would preferably contact a substrate with a reactant in a high ionic strength solution as described above, and then expose the reactant-treated substrate to polymers including any synthetic polymers that contain nucleophiles as described above. For example, in the case of poly(ethylene glycol) (PEG), NH$_2$-PEG-NH$_2$, methoxy-PEG-NH$_2$, methoxy-PEG-SH, SH-PEG-SH, branched-PEG-NH2, and branched-PEG-SH are the polymer structures reacting to SMA-treated surfaces. Alternative forms of polymeric grafting are also envisioned, including free radical graft polymerization, atom-transfer radical polymerization, plasma polymerization/deposition, plasma treatment and surface irradiation, and cationic and anionic monomer or oligomer additions.

Metal Scavenging.

In this embodiment, the amount of metal ions in a fluid can be reduced by binding to reactant-treated substrates or to insoluble DM particles produced by the method. By "reducing" we mean any reduction in the amount of metal ions in solution, preferably to below maximum contaminant levels (MCL) or other established benchmarks for all metals. The DM polymer produced by the method, whether in the form of insoluble particles of a film on a substrate, van be positioned in a solution with metal ions, whereby the surface-modified substrate reduces the amount of metal ion in the solution. The method can be performed in either flow-through or batch mode. See Examples 2 and 3 below for a non-limiting example.

VI. Kits

In an alternate embodiment of the invention, a kit for spontaneously synthesizing the DM polymer is provided. In one embodiment, the kit comprises a salt for making the high ionic strength solution, a reactant as described above dilute, and, optionally, a substrate to be modified or a buffer, and instructions for use.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the SMA solution and substrate be used cooperatively by the recipient.

VII. Examples

The following examples describe various new and useful embodiments of the present invention. While the examples refer to specific coatings, films and particles made with DOPA and methods of using the same, the invention is not limited to the embodiments demonstrated in the examples.

Example 1

High Ionic Strength Formation of DOPA-Melanin Coating for Loading and Release of Antimicrobial Compounds Conformal DOPA-melanin films were formed on a variety of substrates by simple dip-coating in an alkaline DOPA solution at high ionic strength (FIG. 1). Compared to polydopamine, DOPA-melanin coatings have the advantage of high hydrophilicity and also the ability to bind and release cations. We demonstrate the latter by using DOPA-melanin coated polycarbonate to form an antibacterial surface that inhibits and kills S. aureus.

Melanins are widespread in nature, providing pigmentation, photoprotection, anti-oxidant, metal binding and other biological properties.[1] An important subclass of melanins is eumelanin, which forms from tyrosine through a pathway involving 3,4-dihydroxyphenylalanine (DOPA) oxidation, intramolecular cyclization, oligomerization, and aggregation to form an insoluble and heterogeneous solid.[2,3] Research on eumelanins is in part motivated by an interest in understanding structure-property relationships in the context of biological function,[4] but also due to a growing interest in the interesting optical, electrical properties and technological applications of melanin thin films.[5-7]

Synthetic and natural melanins are insoluble in many solvents and this property represents a challenge for processing into useful forms such as thin films. In the past, the deposition of melanin-like thin films on substrates has been accomplished by solution casting,[8,9] (electro)spraying,[10,11] spin coating,[12-14] electrochemical deposition,[7,9,15] and pulsed laser deposition.[16] In addition to generally requiring the solubilization of melanin in organic solvent or aqueous NaOH or ammonia, most reported methods are either line-of-sight, require sophisticated equipment, employ complex multi-step protocols, or can only be performed on conducting substrates. Due to these limitations, there remains a significant need for simple and versatile approaches to melanin thin film deposition. Methods for forming melanin thin films that avoid the need for significant infrastructure and that can accommodate a variety of substrate compositions, shapes and configurations, will accelerate the development of practical applications for this interesting class of bioinspired materials.

A simple and versatile method to modify surfaces with melanin-like coatings was recently reported, involving dip-coating of substrates into an aqueous solution of catecholamine mimics of DOPA-rich mussel adhesive proteins.[17,18] The prototypical catecholamine that has dominated the literature in this field is dopamine, which undergoes auto-oxidation in mildly basic and aerated aqueous solution to form an adherent polydopamine (PDA) film on virtually any substrate.[17] PDA, also referred to as dopamine-melanin because of its chemical similarity to eumelanin, can then act as a primer for further modification leading to numerous applications such as biomolecule immobilization, surface energy modification, biomineralization and biosensing.[19,20] Molecules of interest can also be co-deposited simultaneously with dopamine in a one-step reaction to create surfaces with desired properties.[21]

Several derivatives of dopamine and other catecholamines polymerize in a similar fashion onto a wide variety of substrates. For example, norepinephrine was shown to polymerize into adherent films with the added ability of initiating ring-opening polymerization of ε-caprolactone due to the presence of a hydroxyl group not found on dopamine.[22] Other molecules containing both catechol and amine functionalities have been used to coat various surfaces to enable DNA immobilization[23] and surface polymerization of antifouling brushes.[24]

It would be of interest to spontaneously polymerize DOPA-melanin (DM) films on a variety of substrates in a similar fashion as PDA, as this would further accelerate technological applications of eumelanin-like thin films. In comparison to PDA, DM films would be expected to exhibit a higher concentration of free carboxylic acids that can be exploited for a variety of applications. However, historical reports of the alkaline auto-oxidation of DOPA in water or low ionic strength buffer resulted in a melanin-like product which is soluble[25-27] or a solution-stable supramolecular nanoaggregate.[28] Consistent with this behavior, we as well as others have experienced difficulty forming adherent films from DOPA using the standard conditions developed for spontaneous PDA film formation (buffered aerated $H_2O$, pH 8-9), especially on negatively charged substrates such as $TiO_2$ and $SiO_2$.[29]

Greco et al. reported the spontaneous formation of core-shell melanin particles by autoxidation of DOPA in the presence of cysteinyl-DOPA melanin (CDM).[30] The CDM particle appeared to play a crucial role in DOPA oxidation and epitaxial deposition of the DM shell, and it is therefore unclear if the method could provide a general approach to DM thin film formation on other substrates. A few reports showed the in-situ formation of thin DOPA-melanin (DM) coatings on polymeric membranes to improve wettability[31,32] and to act as a primer for covalent immobilization of molecules,[33-35] however in-situ grown DM films have only been shown to achieve thicknesses of 10 nm or less under conditions that typically yield much thicker films using dopamine. Thus, compared to PDA, the literature demonstrates that DM films are considerably more difficult to grow on substrates by spontaneous autoxidation of DOPA.

In this Example, we report the unexpected finding that spontaneous in-situ autooxidative deposition of DM films proceeds in a facile manner at high ionic strength. Thick adherent DM films formed on a wide variety of substrates, including metal oxide, noble metal and polymer. DM films possess many of the desirable characteristics of PDA films but with some advantages, namely higher hydrophilicity and the ability to electrostatically bind and release cations. The latter property was exploited for fabricating antibacterial coatings by loading and release of a cationic aminoglycoside from DM films.

Figure 2:
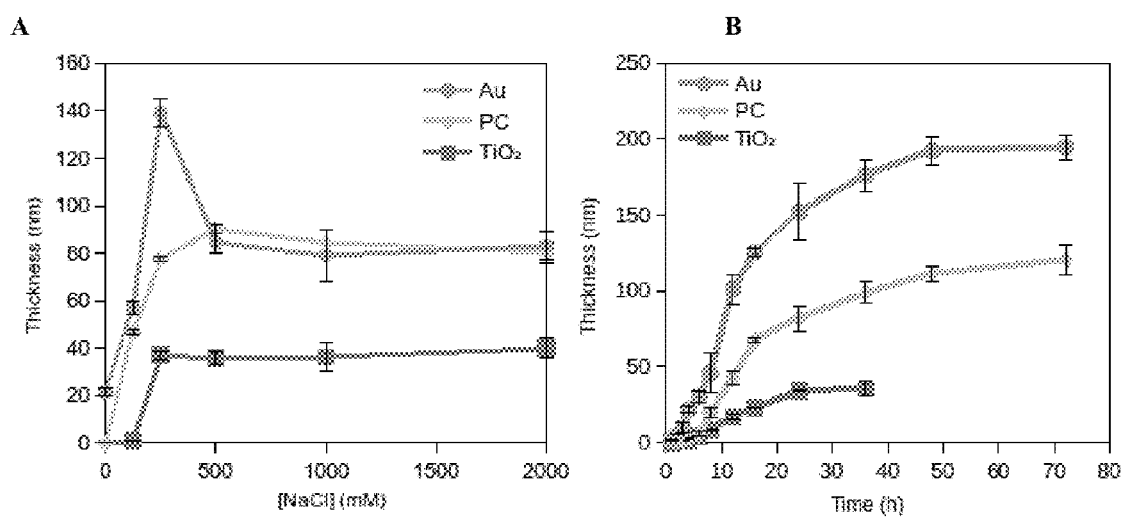
FIG. 2. DM film formation at pH 8.5. (A) Effect of NaCl concentration on DM film thickness after 16 h. (B) Growth of DM film (250 mM NaCl) as a function of time. Reaction schemes I (A) and II (B) of dopamine oxidation.
Figure 3:
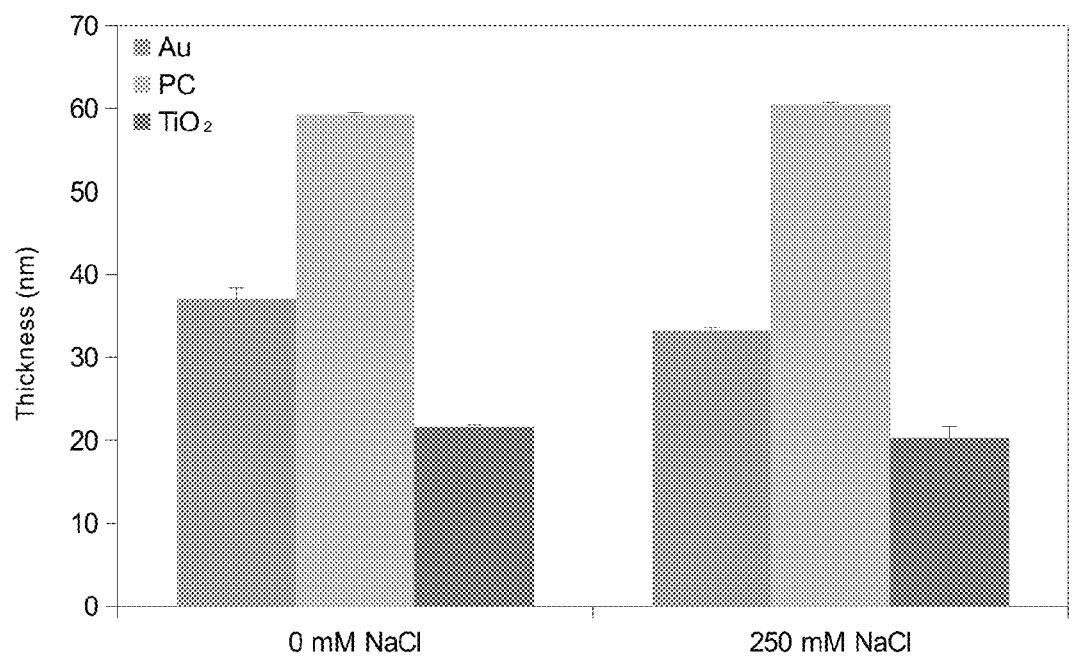
FIG. 3. Thickness of PDA formed after 16 h from 5 mM dopamine in 10 mM bicine pH 8.5, containing 0 or 250 mM NaCl.

The ionic strength dependence of DM film formation was revealed by exposing representative examples of noble metal (Au), oxide ($TiO_2$), and polymer (polycarbonate, PC) to aqueous solutions of DOPA (5 mM) in bicine buffer (10 mM, pH 8.5) at NaCl concentrations from 0-1M and measuring the thicknesses of DM films that formed after 16 h using spectroscopic ellipsometry (FIG. 2A). On PC and $TiO_2$ substrates, DM films were not detected in the absence of NaCl but increased in thickness with increasing ionic strength, plateauing at about 80 nm and 40 nm, respectively, at NaCl concentrations of 250 mM and above. This behavior was in stark contrast to PDA coatings, whose thickness was found to be independent of the NaCl concentration (FIG. 3). DM formation on Au was unusual in that a thin 20 nm film formed without NaCl, rising to 140 nm at 250 mM NaCl before decreasing to about 80 nm upon further increases in NaCl concentration. Although the origin of this anomalous behavior is not known at this time, the observation was reproducible and we hypothesize the phenomenon could be related to electrostatic induction of the Au substrate by the negatively charged DM film. Nevertheless, at 500 mM of NaCl and above, the DM thickness on Au was similar to that on PC (~80 nm).

Figure 4:
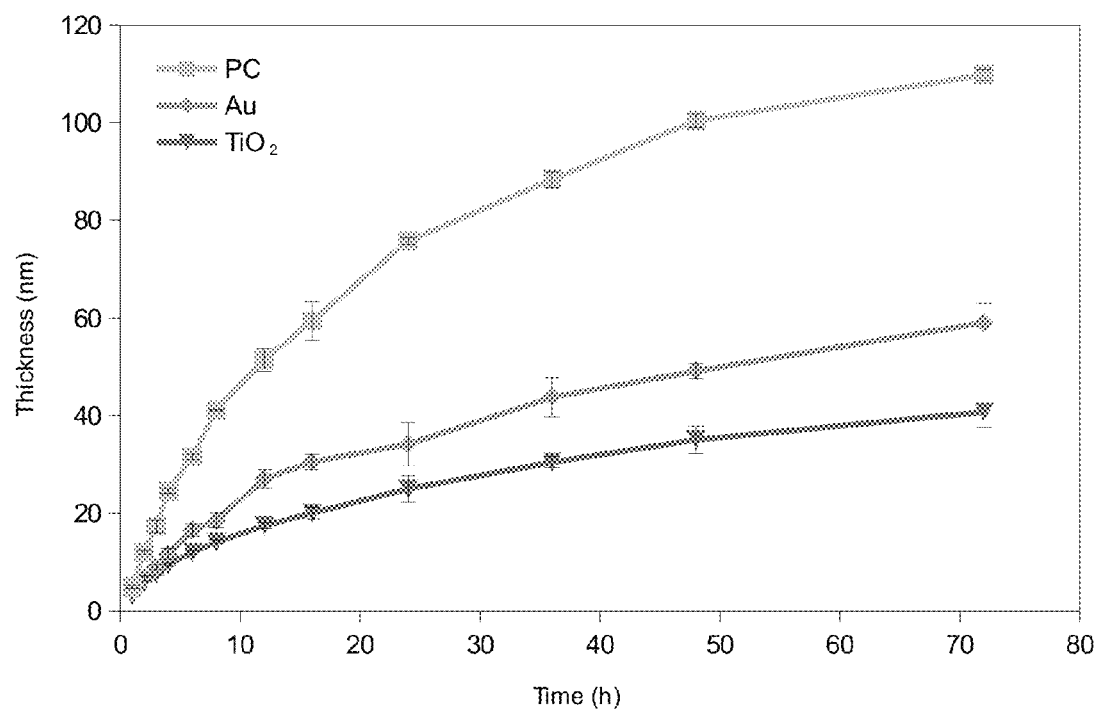
FIG. 4. Time dependence of PDA film growth from 5 mM dopamine, 250 mM NaCl, 10 mM bicine, pH 8.5.
Figure 5:
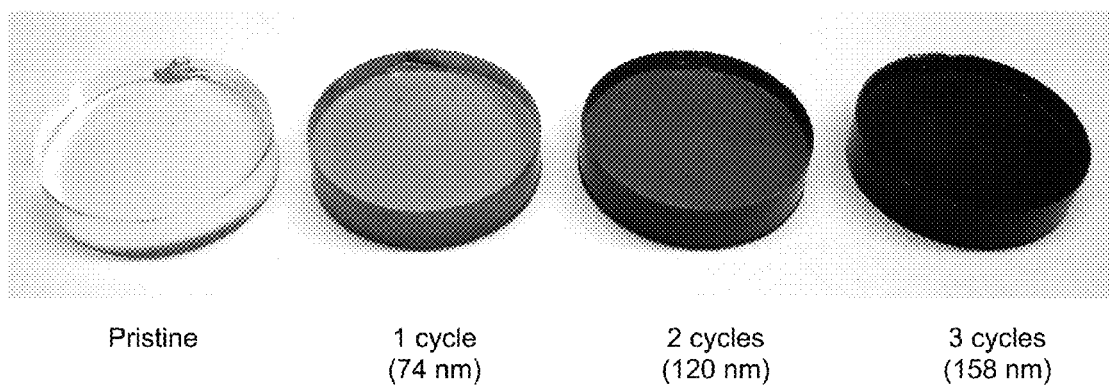
FIG. 5. Photograph of PC substrates coated 0-3 times with DM. Each coating cycle was 20 h from 5 mM DOPA, 250 mM NaCl, 10 mM bicine, pH 8.5. The coating thicknesses are indicated.
Figure 6:
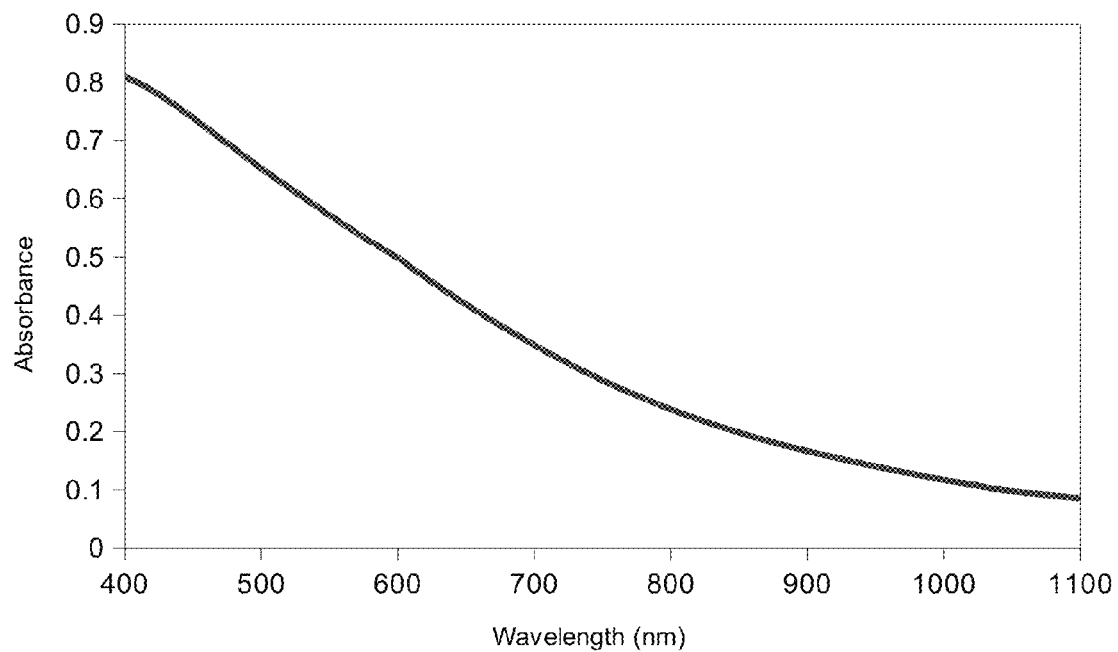
FIG. 6. Broad-band absorption spectrum of DM coated (158 nm thick, both sides) PC substrate.

On the basis of these preliminary results, Buffer A (10 mM bicine, pH 8.5, 250 mM NaCl) was chosen as the optimal buffer for DM formation and was used in a kinetic study to observe the growth of DM films on substrates exposed to 5 mM DOPA. Film growth exhibited a sigmoidal shape, with film thickness growth occurring most rapidly between 8-24 h (FIG. 2B). The DM coatings were conformal and adherent to all substrates tested, although DM grown on $TiO_2$ for longer than 36 h delaminated in patches when rinsed with $H_2O$, perhaps due to electrostatic repulsion between DM and the negatively charged $TiO_2$ surface (the same films did not delaminate when rinsed with 150 mM NaCl). In contrast, PDA formed in Buffer A did not show a sigmoidal growth curve (FIG. 4). Like PDA, DM films appear as dark coatings, depending on the deposition time and thickness (FIG. 5), due to broad-band absorption (FIG. 6) similar to that of eumelanin.[36]

Figure 7:
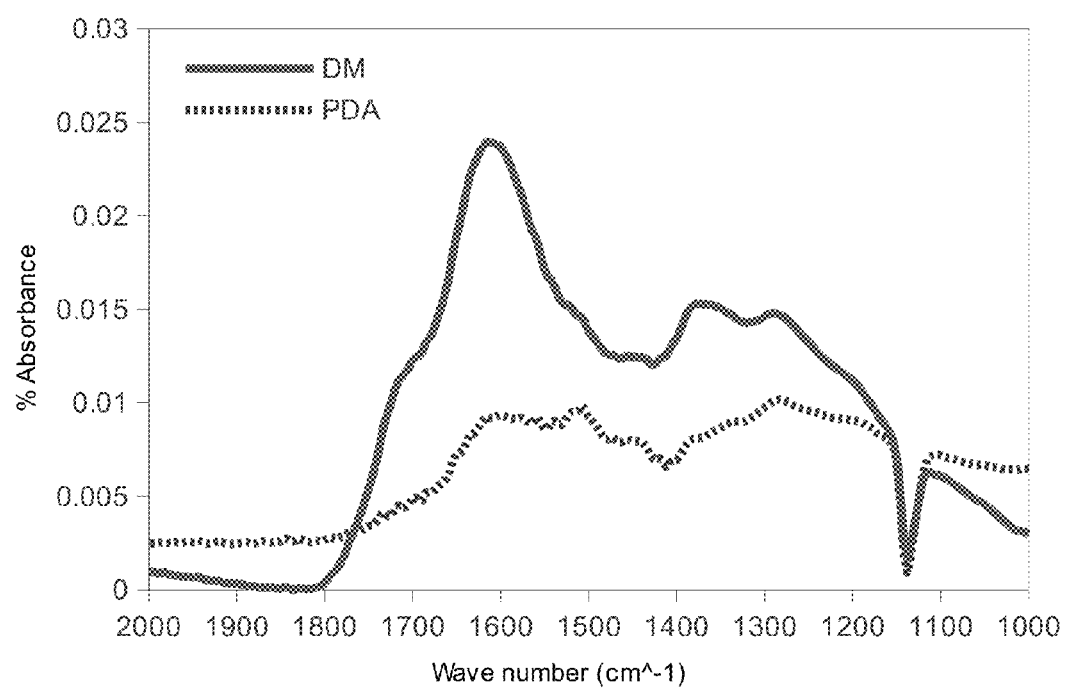
FIG. 7. ATR-FTIR spectra of PDA and DM films deposited on Au, showing the presence of COO⁻ (asymmetric stretching of C—O at 1600 cm⁻¹) and COOH (stretching of C=O at 1700-1730 cm⁻¹) in DM but not PDA.

Fourier transform infrared spectroscopy in attenuated total reflection mode (ATR-FTIR) was used to compare the differences in functional groups between DM and PDA films deposited on Au. A major distinction between DM and PDA was the presence of peaks at 1600 $cm^{-1}$ and a shoulder at 1700-1730 $cm^{-1}$, corresponding to $COO^-$ (asymmetric stretching) and COOH (stretching), respectively (FIG. 7).[37] These data suggest that carboxylic acid groups are present in DM and exist in both the protonated and carboxylate form.

X-ray photoelectron spectroscopy (XPS) was used to further characterize the DM coating formed after 16 h. Compared to the pristine substrates, DM modified substrates exhibited increased N content, reaching a N/C ratio similar to the 0.11 theoretical N/C ratio of DOPA (Table 2). O/C ratios were found to be less than or equal to the 0.44 theoretical O/C ratio of DOPA. Importantly, substrate-specific signals such as Au and Ti were either eliminated or drastically reduced, suggesting the formation of an adventitial DM film thicker than the typical XPS analysis depth (~10 nm). We also noted the presence of about 3% Na in all the DM films, likely due to the presence of Na-carboxylate salts as suggested by the FTIR data.

TABLE 2

Atomic compositions of substrates as measured via XPS before modification, after DM coating (16 h in 5 mM DOPA, 250 mM NaCl, 10 mM bicine, pH 8.5) and after GM loading.

| | Atomic Composition (%) | | | | | Ratios | |
|---|---|---|---|---|---|---|---|
| | C | O | N | Na | Au/Ti | O/C | N/C |
| Au | 53.6 | 8.6 | — | — | 37.8 | 0.160 | — |
| + DM | 64.7 | 24.0 | 7.3 | 3.9 | — | 0.371 | 0.113 |
| + Gentamicin | 67.9 | 22.7 | 9.4 | — | — | 0.334 | 0.139 |
| $TiO_2$ | 29.8 | 52.2 | 0.7 | — | 17.3 | 1.752 | 0.023 |
| + DM | 60.9 | 27.3 | 6.5 | 3.5 | 1.7 | 0.449 | 0.107 |
| + Gentamicin | 63.1 | 26.8 | 8.5 | — | 1.6 | 0.424 | 0.134 |
| PC | 85.6 | 14.4 | — | — | — | 0.168 | — |
| + DM | 65.7 | 23.9 | 7.1 | 3.3 | — | 0.364 | 0.108 |
| + Gentamicin | 67.6 | 23.7 | 8.8 | — | — | 0.350 | 0.130 |
| DOPA (theoretical) | 64.3 | 28.6 | 7.1 | — | — | 0.444 | 0.111 |
| Gentamicin (theoretical) | 63.6 | 21.2 | 15.2 | — | — | 0.333 | 0.238 |

Dashes indicate elements present below the detection limit.

Figure 8:
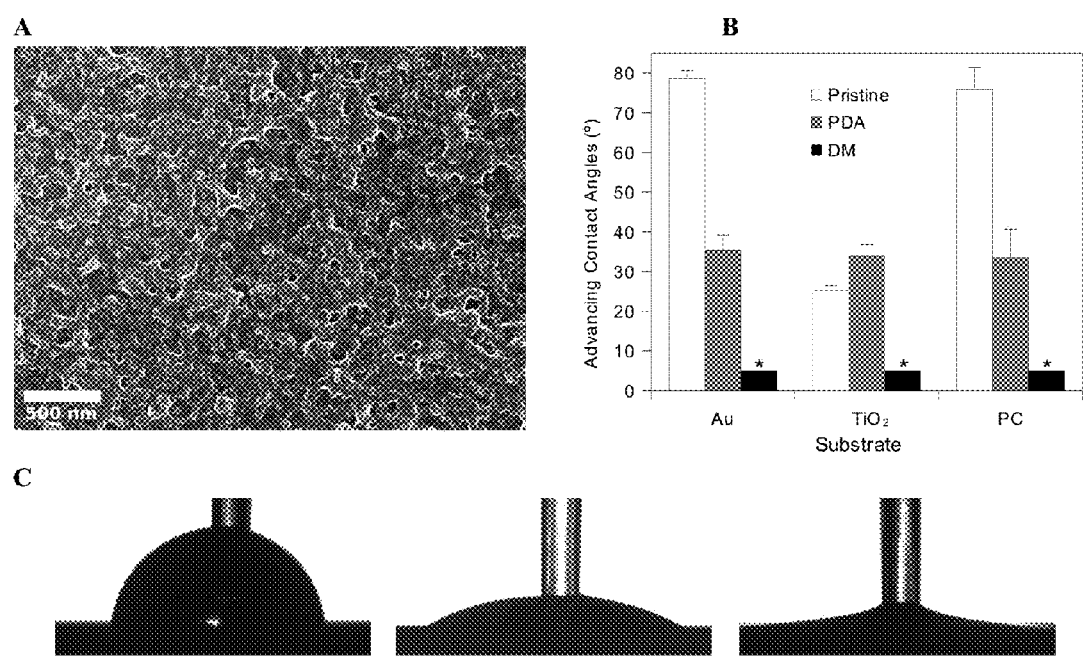
FIG. 8. Surface morphology and wetting properties of DM films. (A) SEM image of 23 nm thick DM on $TiO_2$ formed after 16 h. (B) Advancing water contact angles of DM and PDA formed after 16 h on various substrates. * indicates angles less than 10°. (C) Images of advancing water droplet on pristine PC, PC coated with PDA, and PC coated with DM, respectively.

Scanning electron microscopy of DM-coated $TiO_2$ revealed that the DM film obscured the underlying substrate and possessed a rough or porous surface (FIG. 8A). All three DM modified substrates were almost completely wetting (<10°), which we attribute to the presence of a high density of ionized carboxylate groups. In contrast, the advancing contact angles of PDA-modified substrates were about 35° (FIGS. 8B-C), which is consistent with the literature.[17]

Like PDA, the ability of DM films to adhere to different classes of substrates is likely related to the presence of the catechol functional group, as it is capable of participating in a wide variety of interactions, such as metal coordination, hydrogen bonding and π stacking.[38] The structure of PDA has been the subject of several recent reports.[39-41] One hypothesis is that PDA has a structure related to eumelanin, which is commonly believed to consist of 5,6-dihydroxyindole (DHI) and 5,6-dihydroxyindole carboxylic acids (DHICA) as subunits.[36] Recent work by Vecchia et al. suggests that dopamine first oxidizes at high pH into its quinone, which then reacts via multiple pathways resulting in a complex product containing subunits of uncyclized dopamine, DHI cyclized from dopamine, and pyrrolecarboxylic acid moieties.[40]

Figure 9:
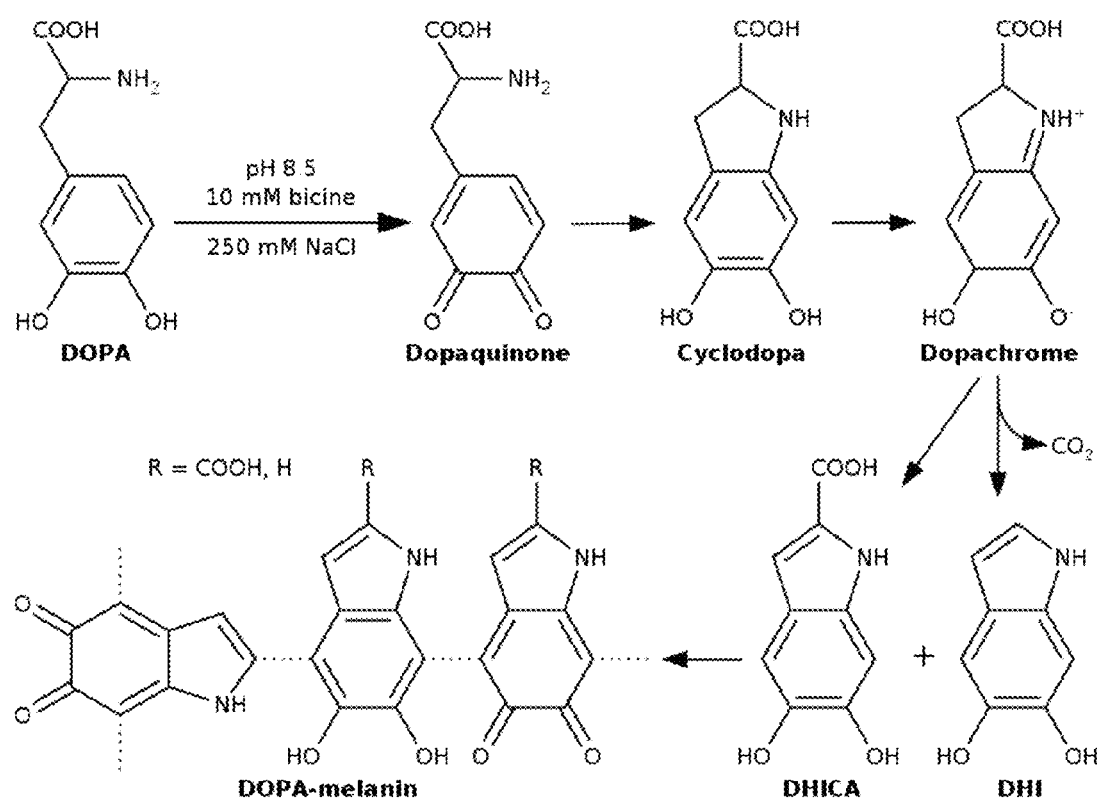
FIG. 9. Proposed pathway of DM film formation based on current understanding of melanogenesis, with the final product consisting of a mixture of DHICA and DHI subunits with various possible linkages and oxidative states.

As DOPA is a precursor of natural eumelanin, the formation of DM (FIG. 9) is expected to more closely mimic biological melanogenesis which involves enzyme mediated DOPA oxidization into dopaquinone, cyclization into cyclodopa, conversion into dopachrome, rearrangement by dopachrome tautomerase (DCT) into DHICA and DHI, which then undergo oxidative polymerization into eumelanin.[42] In the absence of DCT, the majority of dopachrome undergoes decarboxylation to form DHI instead of DHICA.[43] In contrast, our FTIR and XPS data suggests that a significant presence of carboxylic acid is preserved in DM films formed in high salt buffer. It is possible that charge screening of the deprotonated carboxylates of DOPA and its derivatives at high ionic strength leads to an increase in aggregation and surface binding. The exact composition of DM films, presence of uncyclized DOPA subunits, linkages between subunits, and their oxidation states are still unknown and will require further investigation.

Figure 10:
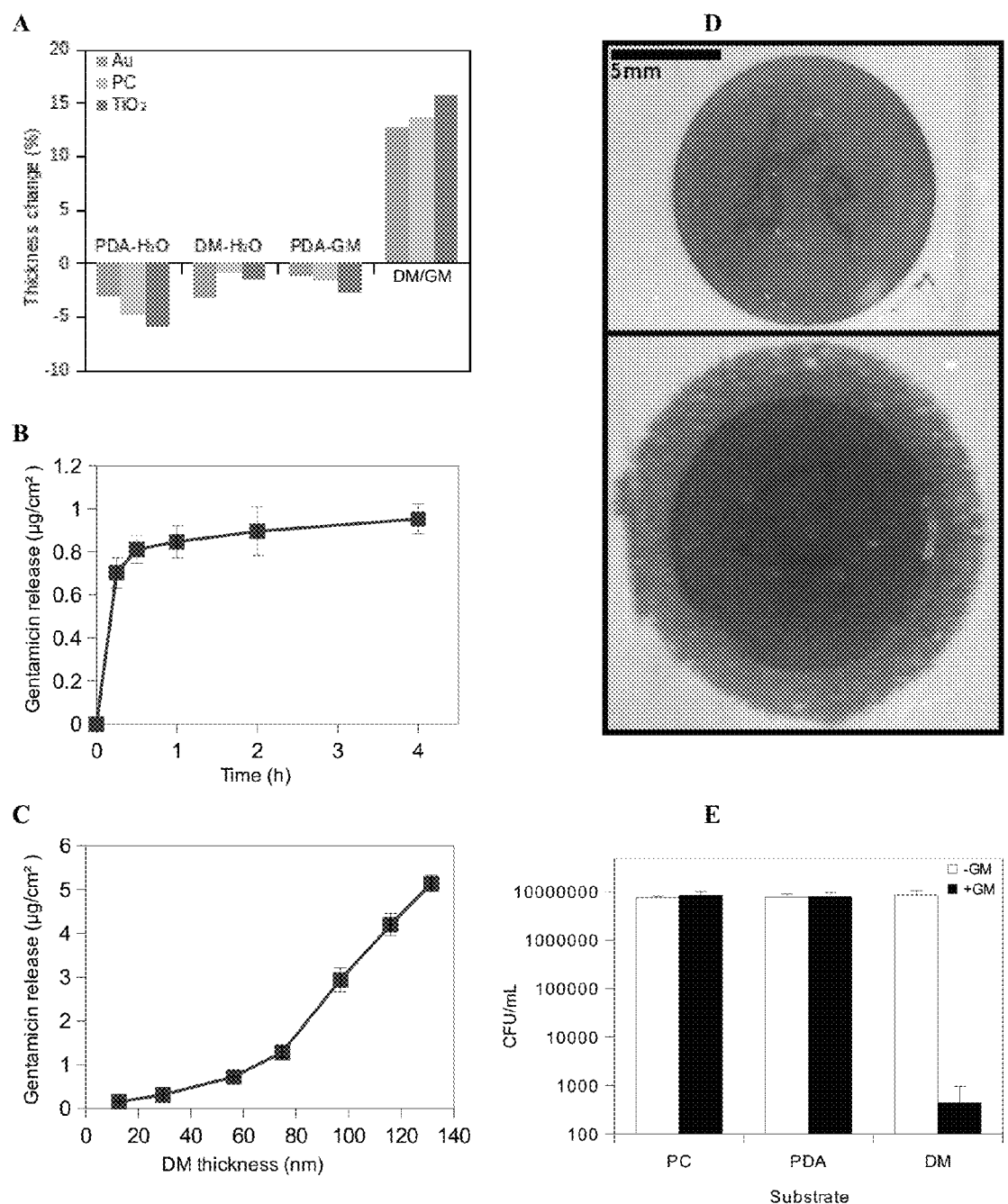
FIG. 10. Binding and release of a cationic antibacterial compound from DM films. (A) Percentage thickness change of DM or PDA after 16 h exposure to $H_2O$ or GM solution. (B) GM release from PC/DM/GM over 4 h. (C) 4 h GM release from PC/DM/GM as a function of DM film thicknesses. (D) Zones of inhibition of $S.$ $aureus$ after 18 h incubation of PC coated with DM/GM (bottom) or PDA/GM (top). (E) Death assay showing survival of planktonic $S.$ $aureus$ after 4 h exposure to PC coated with PDA and DM.

To illustrate a functional advantage afforded by residual carboxylic acids in DM compared to PDA, DM films were exploited for binding and release of the cationic aminoglycoside gentamicin (GM). GM is effective against a wide spectrum of bacteria, including methicillin-resistant *Staphylococcus aureus* (MRSA)[44] which is one of the largest causes of nosocomial infections leading to high morbidity and mortality.[45] Substrates were coated with DM or PDA and then immersed in either $H_2O$ or a GM solution (5 mg/mL in $H_2O$) for 16 h. Thickness measurements revealed that both DM and PDA films on all substrates decreased in thickness by about 1-5% in $H_2O$, which we surmise may be due to loss of loosely bound DM and PDA (FIG. 10A). In GM solution, PDA films decreased in thickness by a similar amount (1-3%) whereas DM films on all the three substrates swelled by about 10-15%. XPS revealed that loading of GM into DM-coated substrates resulted in an increase in N/C ratio and a decrease in the O/C ratio, which is consistent with the incorporation of GM into the DM films (Table 1). Additionally, the virtual loss of Na signal suggests that GM had been incorporated via cationic substitution for $Na^+$ ions which were initially associated with the carboxylates in the DM film. These results suggest that GM loaded into DM but not significantly into PDA.

Figure 11:
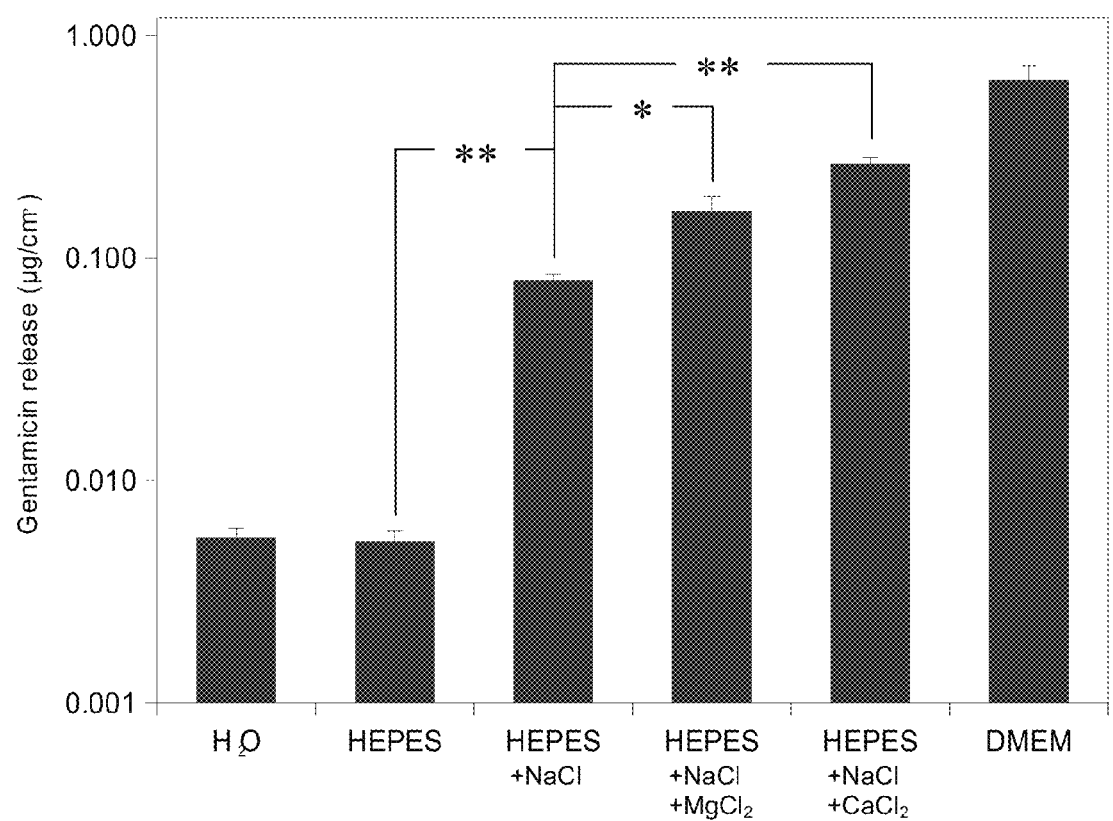
FIG. 11. Release of gentamicin from DM/GM coating in $H_2O$, HEPES (10 mM, pH 7.4), HEPES with NaCl (150 mM), HEPES with NaCl and $MgCl_2$ (0.814 mM), HEPES with NaCl and $CaCl_2$ (1.8 mM), and DMEM (155 mM Na⁺, 0.814 mM $Mg^{2+}$, 1.8 mM $Ca^{2+}$) as measured via ELISA. (* and ** indicates $p<0.05$ and $p<0.01$ respectively.)

The release of GM from DM was investigated by immersing coated PC substrates (PC/DM/GM) into Dulbecco's Modified Eagle Medium (DMEM) and measuring GM release using an enzyme-linked immunosorbent assay (ELISA). As shown in FIG. 10B, a 56 nm thick DM film released 0.95 μg/cm² of GM over 4 h. The total amount of GM loaded and released from DM films could be tuned easily by varying the DM thickness (FIG. 10C), which in turn was controlled by coating time or by multiple coating cycles with rinsing and drying in between steps, a method which had previously been shown to form thicker PDA films.[46] The composition of inorganic salts in the release medium was found to influence GM release (FIG. 11), suggesting that $Na^+$, $Mg^{2+}$ and $Ca^{2+}$ found in DMEM play a role in GM release.

A Kirby-Bauer disk diffusion assay was performed to evaluate the ability of GM-loaded DM films to inhibit *S. aureus* growth. Coated and uncoated PC substrates were placed onto agar plates that were inoculated with *S. aureus* and incubated for 18 h. As shown in FIG. 10D, incubation with DM/GM resulted in a zone of inhibition of 16.7 mm, indicating that GM was released from the coating to inhibit bacterial growth away from the substrate. In contrast, bare PC, PC treated with GM (PC/GM), PDA, PDA/GM, and DM did not show any zones of inhibition (Table 3).

TABLE 3

Substrate diameters and zones of inhibition of *S. aureus* inoculated agar plates after 18 h incubation with substrates with various coatings.

| | Diameters (mm) | |
|---|---|---|
| Substrate | Original | ZOI |
| PC | 12 | N/D |
| PC/GM | 12 | N/D |
| PDA | 12 | N/D |
| PDA/GM | 12 | N/D |
| DM | 12 | N/D |
| DM/GM | 12 | 16.7 ± 0.6 |
| 10 μg GM Disk | 6 | 19.5 ± 1.0 |

N/D = none detected.

To show that GM-loaded DM was not only bacteriostatic but also bactericidal, we performed a death assay in which planktonic *S. aureus* were incubated with substrates for 4 h followed by enumeration of surviving bacteria. Bacteria exposed to GM-loaded DM exhibited substantial bacterial killing, whereas all other coatings had statistically similar survival rates as bare PC (FIG. 10E). Together, these experiments demonstrated that only DM films were able to load and release sufficient GM to inhibit and kill *S. aureus*, illustrating a significant advantage of DM over PDA that is likely correlated to the presence of carboxylate groups in DM.

In conclusion, we have developed a facile substrate-versatile surface modification technique that exploits high ionic strength to polymerize DOPA into thick adherent DM films under aqueous, mildly alkaline conditions. Spontaneous deposition of DM films by immersion coating represents a noteworthy simplification compared to previously employed DM coating methods, affording an expansion in the range and configuration of substrates capable of supporting DM films. Compared to PDA films that have been more extensively studied, DM films exhibit enhanced wettability and can be loaded with cationic guest molecules. This was exemplified by demonstrating loading and release of GM from DM films to kill *S. aureus* and will foreseeably work with a wide variety of other cationic aminoglycosides. The ease of formation and reversible cation-binding properties of DM films may lead to new applications of catecholamine coatings for preventing bacterial colonization of surfaces.

Experimental

DOPA and Dopamine Polymerization

L-DOPA (10 mM) was first dissolved in $H_2O$, then mixed in equal volumes with 2× Buffer A (10 mM bicine, pH 8.5, 250 mM NaCl). Dopamine.HCl (5 mM) was directly dissolved in Buffer A. Substrates were placed into a 24-well plate and immersed in the DOPA or dopamine solutions for desired times, before thorough rinsing with $H_2O$ and blow-drying with $N_2$. PC samples were allowed to float via surface tension, face down.

GM Loading and Release:

Substrates coated with PDA or DM were exposed to a 5 mg/mL GM solution in $H_2O$ overnight (16 h) before rinsing with $H_2O$ and blow-drying with $N_2$. GM loaded substrates were placed into 24-well plates containing 1 mL of DMEM. GM concentration in the release solution was measured using ELISA (Bioo Scientific, TX).

Characterization:

The thicknesses of all films were measured using an ESM-300 spectroscopic ellipsometer (J. A. Woollam, Lincoln, Nebr.) at multiple angles of incidence using wavelengths from 400 to 1000 nm. PDA and DM layers were fit to the refractive index and thickness of a Cauchy model with initially fixed coefficients ($A_n$=1.45, $B_n$=0.01). SEM was performed on 5 nm Os coated samples at 10 kV using a Hitachi SU8030.

Bacteria Inhibition and Death Assays:

PC substrates were coated for 20 h twice with DM (~90 nm) or PDA (~80 nm) and then loaded with GM as described above. *S. aureus* (ATCC 29213) was expanded overnight in tryptic soy broth (30 g/L) and centrifuged twice at 4000 rcf for 5 min with saline rinses. For the Kirby-Bauer assay, bacteria were resuspended to $10^8$ CFU/mL in 150 mM saline, of which 100 µL was spread onto 4 mm thick cation-adjusted Müller-Hinton (CAMH) agar. The test samples (12 mm diameter round PC) were placed onto the agar for incubation (18 h, 35° C.) before measuring zones of inhibition. GM disks (10 µg GM, 6 mm diameter, BD, NJ) were used for positive control. For the death assay, the bacteria were resuspended at $10^7$ CFU/mL in DMEM (ATCC) with 10% calf bovine serum (ATCC), of which 100 µL was exposed to each substrate in 24-well plates. The positive control was the same bacterial solution with 50 µg/mL of GM. After 4 h incubation (37° C., 5% $CO_2$), the well plates were sonicated for 2 min to release any adhered bacteria, the bacterial solution was serially diluted and plated on CAMH agar. Enumeration was performed after 24 h incubation (37° C., 5% $CO_2$).

All reagents were purchased from Sigma-Aldrich unless noted otherwise. $H_2O$ was purified ($\geq$18MΩ) using Barnstead Nanopure (Thermo Scientific). Si wafers were coated with Au by thermal evaporation (Lesker Nano-38), or with $TiO_2$ by electron beam evaporation (Edwards Auto 500). PC (Makrolon GP) substrates were purchased from McMaster-Carr (Elmhurst, Ill.). All substrates were cut to 1×1 cm and cleaned by sonicating for 10 min sequentially in 5% Contrad-70, $H_2O$ and IPA.

XPS was performed on an ESCALab 250Xi (Thermo Scientific) with spectra calibrated using the C(1s) peak (284.6 eV). ATR-FTIR data was collected using a Thermo Nicolet Nexus 870 equipped with a ZnSe ATR crystal. XPS and ATR-FTIR analysis were performed at the Nuance Keck-II facility of Northwestern University.

Example 2

High Ionic Strength Formation of DHICA-Rich DOPA-Melanin Particles for Toxic Heavy Metal Removal In this Example, we investigate the formation of insoluble DM particles using high ionic strength buffers, apply them for heavy metal binding, and compare their binding performance with AC, PDA particles and other forms of melanin. We show that the type and concentration of salt used in the polymerization solution has a significant effect on the ratio of the DHICA to DHI subunits of the DM, which correlates with the ability of the DM to bind heavy metals.

Heavy metal contamination of drinking water in both developing and developed countries is a major concern. In particular, lead contamination is a serious issue due to its toxic effects on children and unborn fetuses. Eumelanin, the ubiquitous biological pigment, has been noted for its high binding affinity with heavy metal ions. However, synthetic eumelanin has not been utilized as an agent for heavy metal ion removal, in part due to it being soluble. In this Example, we show that high ionic strength alkaline buffers can be used to autoxidize DOPA, resulting in the formation of insoluble particles of DOPA-melanin with high DHICA content. We then show that DHICA content of melanin correlates with the binding capacities for Pb(II), Cd(II), Cu(II) and Hg(II). In particular, DOPA-melanin formed using $MgCl_2$ alkaline buffer was found to have higher binding capacities for the stated heavy metal ions than natural sepia melanin. These findings show that synthetic DOPA-melanin formed at high ionic strength can be an excellent material to use for heavy metal remediation.

Millions of people around the world do not have access to clean drinking water despite it being a basic human right.(1) In developing countries with poor regulations, industrial wastes containing heavy metals such as lead, cadmium and mercury continue to contaminate the water supply.(2) Even in developed countries, the continued use of lead pipes can sometimes cause dangerous lead levels in tap water.(3) Even low blood lead levels have an adverse effect on the intellectual development of children(4) and chronic exposure are linked to a variety of health problems such as muscle tremors and weakness, hypertension, neurobehavorial disorders, and kidney diseases.(5, 6) The recent lead contamination in the tap water of Washington D.C. has resulted in dangerous lead blood levels in the local children (7) and has also been linked to an increase in fetal death.(8)

Melanins are dark pigments ubiquitous in animals and plants, that serve a wide variety of functions such as photoprotection, antioxidation, and metal binding.(9) The main classes of melanins are eumelanin, pheomelanin, and neuromelanin. Eumelanin is a black or brown polymer that consists of 5,6-dihydroxyindole (DHI) and 5,6-dihydroxyindole carboxylic acid (DHICA) subunits, and are the major pigment found in the skin, hair and eyes of humans. In biological melanogenesis, tyrosine is oxidized by tyrosinase into dopaquinone, followed by cyclization and conversion into dopachrome, which either spontaneously decarboxylates into DHI or enzymatically rearranged into DHICA by dopachrome tautomerase. DHI and DHICA then undergoes further oxidative polymerization and aggregation to form eumelanin.(10) Pheomelanin, a yellow or red pigment that gives red hair its color, consists of benzothiazine and benzothiazole subunits. Pheomelanin formation branches off from eumelanin formation after dopaquinone, and involves reaction with cysteine to form cysteinyldopas which undergoes further reactions to form the subunits of pheomelanin. (10) Neuromelanin is found in the substantia nigra and is distinct from eumelanin in that it forms from dopamine via auto-oxidation instead of enzymatic activity, and hence would contain mostly DHI instead of DHICA subunits.(11)

Melanins have been noted for their ability to bind to heavy metal ions with high affinity, even higher than the chelating agent EDTA for some metals.(12-14) Neuromelanin, in particular, has been hypothesized to serve a neuroprotective role by chelating heavy metals.(15, 16) In fact, the loss of neuromelanin has been associated with Parkinson's disease. (11) Dopamine-melanin, formed via autoxidation of dopamine at alkaline pH, has been used as a synthetic model of neuromelanin.(17, 18) We recently found that dopamine-melanin also forms as conformal coatings on virtually any substrate simply by dip-coating in an alkaline aqueous solution of dopamine.(19) This coating has become widely known as polydopamine (PDA) and has been demonstrated to be useful in myriad applications in diverse fields.(19) One application of PDA is in heavy metal remediation. PDA coated glass beads were found to bind heavy metals with capacities several times that of activated carbon (AC), which has been an industry standard for heavy metal removal.(20) PDA particles and PDA-functionalized graphene hydrogels have also been used for the same purpose.(21, 22)

Figure 12:
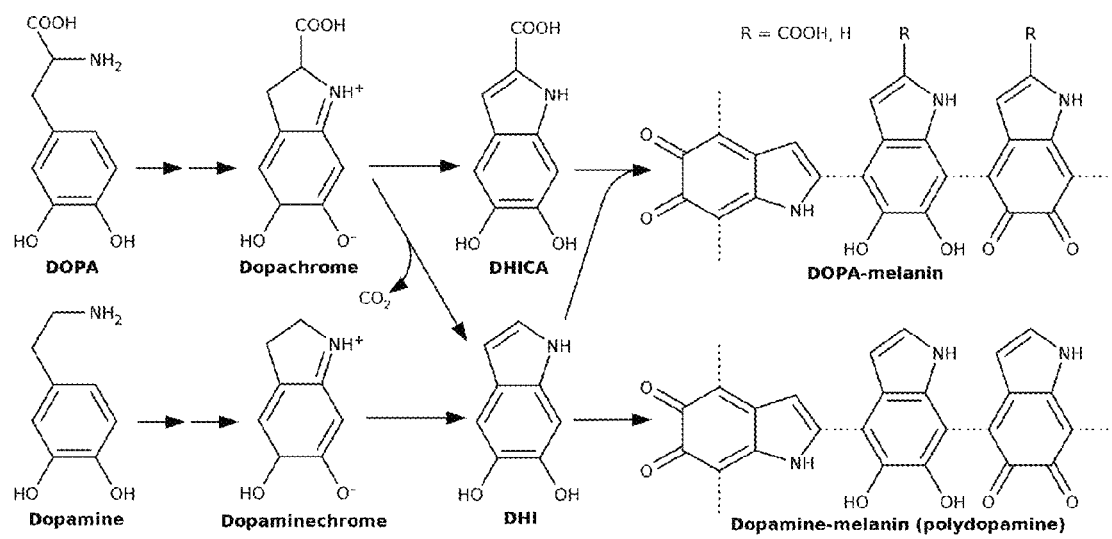
FIG. 12. Comparison of DM and PDA formation, showing that DM contains both DHICA and DHI subunits while PDA contains only DHI subunits.

As PDA is formed from dopamine, it contains mainly DHI, and lacks DHICA which can only form with DOPA as a starting molecule.(23) PDA is believed to bind to heavy metals through the catechol and amine of the DHI subunit. (20) In contrast, synthetic melanin formed from DOPA would contain both DHI and DHICA subunits (FIG. 12). Since DHICA contains an additional carboxylic acid in comparison to DHI, one would expect synthetic DOPA-melanin (DM) to bind heavy metals with increased capacity and affinity. However, there are few reports of the use of DM in heavy metal remediation, and we believe this is due to the fact that DM formed via autoxidation of DOPA in an alkaline buffer remains soluble above pH 3.(17, 24) In comparison, PDA formed in the same buffer precipitates easily and hence are amenable for physical separation after heavy metal binding.(17) Additionally, DM does not form coatings like PDA does, especially on negatively charged substrates like metal oxides.(25) We hypothesized that this is due to the repulsion of the negative charges of the carboxyl of DHICA during formation, limiting polymerization and/or aggregation, and showed that by using high ionic strength buffers, the charges can be screened to allow formation of DM films on various substrates, which also had the ability to load and release a cationic drug through electrostatic binding (see Example 1 above)

Materials.

10,000 ppm solutions of Pb(II), Cu(II), Cd(II) and Hg(II) were purchased from Inorganic Ventures (Christiansburg, Va.). L-DOPA, dopamine HCl, and all other chemicals used were purchased from Sigma (St. Louis, Mo.).

Synthesis of Melanins.

DOPA or dopamine (10 mM) was dissolved in the buffer (20 mM bicine, 500 mM NaCl, pH 8.5). The solution was allowed to react overnight (20 h) at room temperature in an open bottle with shaking for access to air. The solution was then centrifuged at 4500 rcf for 5 mins, the supernatant was decanted, and the pellet was resuspended in $H_2O$. This washing step was repeated about 10 times until the supernatant was clear. The pellet was then resuspended in 5 mL of $H_2O$, frozen with liquid nitrogen, lyophilized for 3 days, and equilibrated with atmospheric moisture for 1 day. DM was also formed in bicine buffers containing 125-1000 mM of either NaCl, KCl, $MgCl_2$, or $CaCl_2$ with the pH adjusted to 8.5 after addition of the salt.

Alkaline Peroxide Degradation Assay.

The melanins were degraded using an established protocol (26) with minor modifications. Briefly, 0.1 mg of melanin was suspended in 100 μL of H2O, mixed with 375 μL 1M $K_2CO_2$ and 25 μL 30% $H_2O_2$, and shaken at room temperature for 20 h. Following that, the residual $H_2O_2$ was decomposed by adding 50 μL 10% $Na_2SO_3$, and the mixture was acidified with 140 μL 6M HCl. 80 μL samples were analyzed using RP-HPLC using a C18 column at 50° C. with flow rate of 0.7 mL/min, and the absorption at 269 nm was monitored and used for quantification. PTCA and PDCA solutions at various concentrations were used for calibration.

Metal Ion Binding.

All metal ion solutions were prepared from 10,000 ppm stock to their desired concentration and pH adjusted to 4.8 for Pb, Cu and Cd, and 3.6 for Hg. 5 mg of each sample was mixed with 10 mL of the metal ion solution in a 15 mL metal-free centrifuge tube. Following 3 h of equilibration on a rocker at room temperature, the tubes were centrifuged at 4500 rcf for 5 mins. The supernatant was then passed through a 0.22 μm filter and analyzed using inductively coupled plasma mass spectrometry (ICP-MS) at known dilutions for its metal concentration. The metal bound by the melanins were then inferred from the reduction in metal concentration of the supernatant.

Scanning Electron Microscopy.

PDA and DM particles were suspended in $H_2O$, dropped onto 1×1 cm silicon wafers and allowed to dry. The samples were then coated with 5 nm osmium and imaged using a Hitachi SU8030 scanning electron microscope at 10 kV.

PDA and DM Synthesis.

PDA particles were synthesized by dissolving dopamine (10 mM) in pH 8.5 bicine buffer (20 mM) and stirring for 20 h. The PDA particles formed were easily collected via centrifugation and were stable to $H_2O$ rinses. In contrast, when attempting to synthesize DM particles in the same buffer from DOPA, the DM that has formed remained soluble and could not be centrifuged out. Chio et al. previously described this observation, and noted that in order to precipitate the DM after formation, a decrease in pH to below 3 (to protonate the carboxyls) or the use of salts such as sodium chloride or ammonium sulfate was required. (24) However, we found that the DM formed and then precipitated using acidification or salt resulted in DM particles which redissolved when resuspended in pure $H_2O$.

Figure 13:
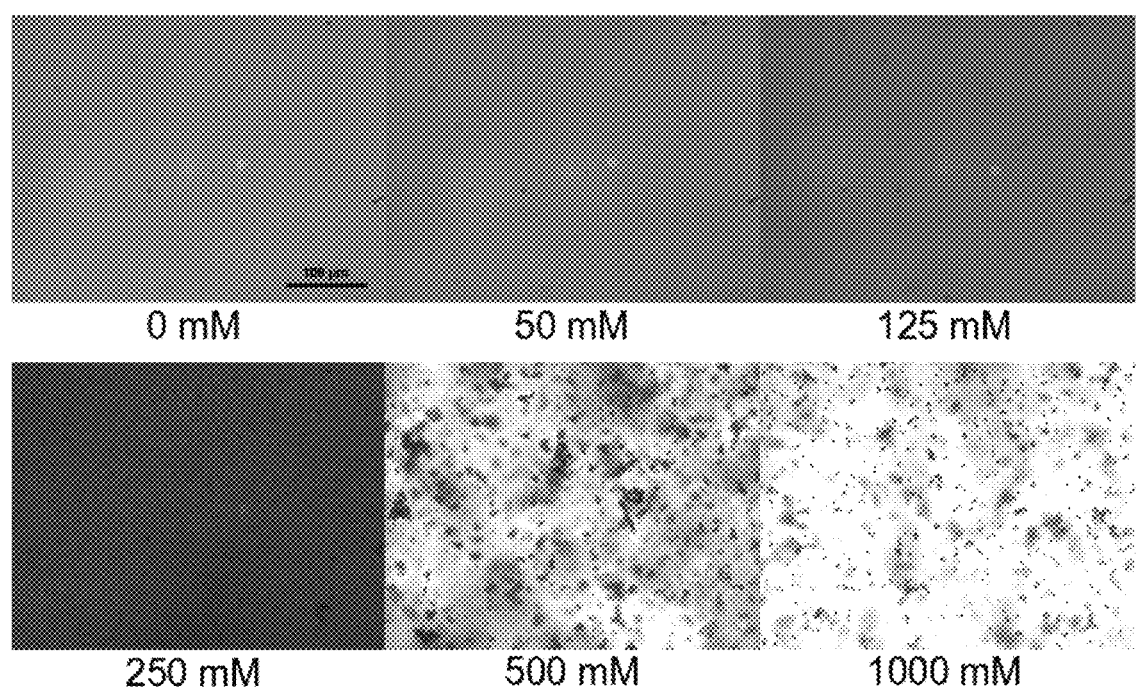
FIG. 13. Optical micrographs of 5 mM DOPA in 10 mM bicine pH 8.5 buffer with varying NaCl concentration after 16 h, showing DM particle formation for 250 mM NaCl and above.

Instead of using salt only to precipitate DM after formation, we investigated the effect of having salt present in the buffer during DM formation. DOPA was allowed to autoxidize in pH 8.5 buffer with various concentrations of NaCl overnight (20 h), and the solutions were observed using optical microscopy. As shown in FIG. 13, no visible particles were formed in buffers containing up to 125 mM NaCl, although the solutions did become increasingly darker. Beginning at 250 mM NaCl, small particles appeared, and at 500 mM-1000 mM NaCl, larger particles precipitated. The DM that were formed at 500-1000 mM NaCl buffers could be collected through centrifugation and washed in pure $H_2O$ without requiring acidification. This suggests that having salt present during DM formation increases its polymerization or aggregation, resulting in larger particles, likely by reducing the electrostatic repulsion of DHICA.

Figure 14:
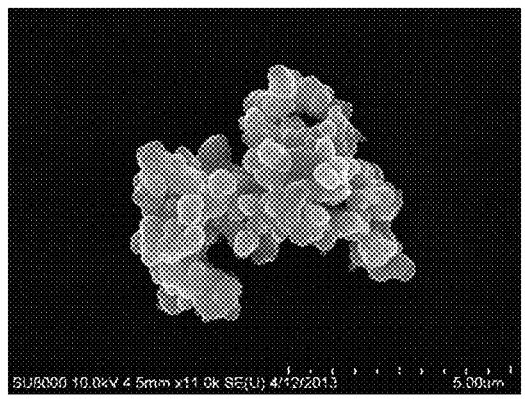
FIG. 14. SEM of PDA (top row) and DM formed using 500 mM NaCl bicine buffer (bottom row).
Figure 14:
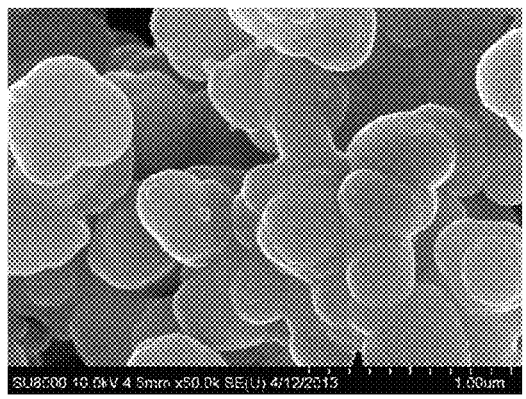
Figure 14:
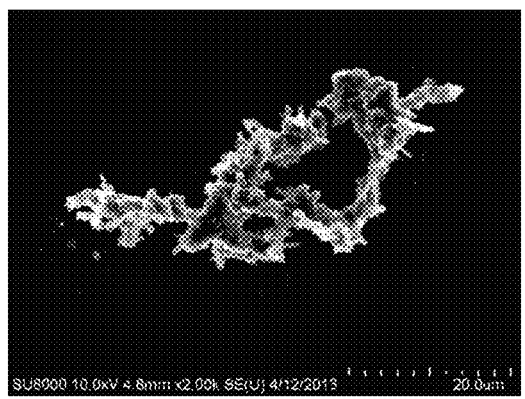
Figure 14:
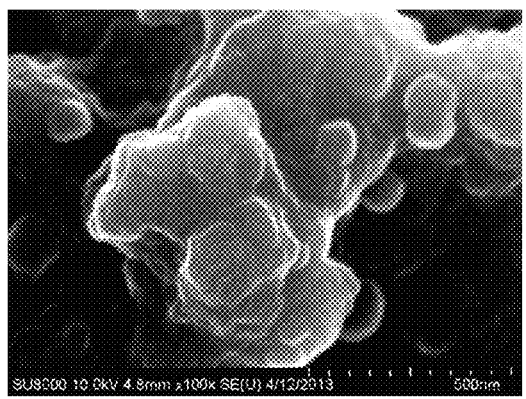

Scanning electron microscopy revealed that PDA particles were about 5 μm in diameter, and seemed to be fused together from smaller particles about 500 nm in diameter. DM particles were much larger, measuring 40 μm across, and also contained sub-micron features on its surface (FIG. 14).

PTCA/PDCA Ratios.

Figure 15:
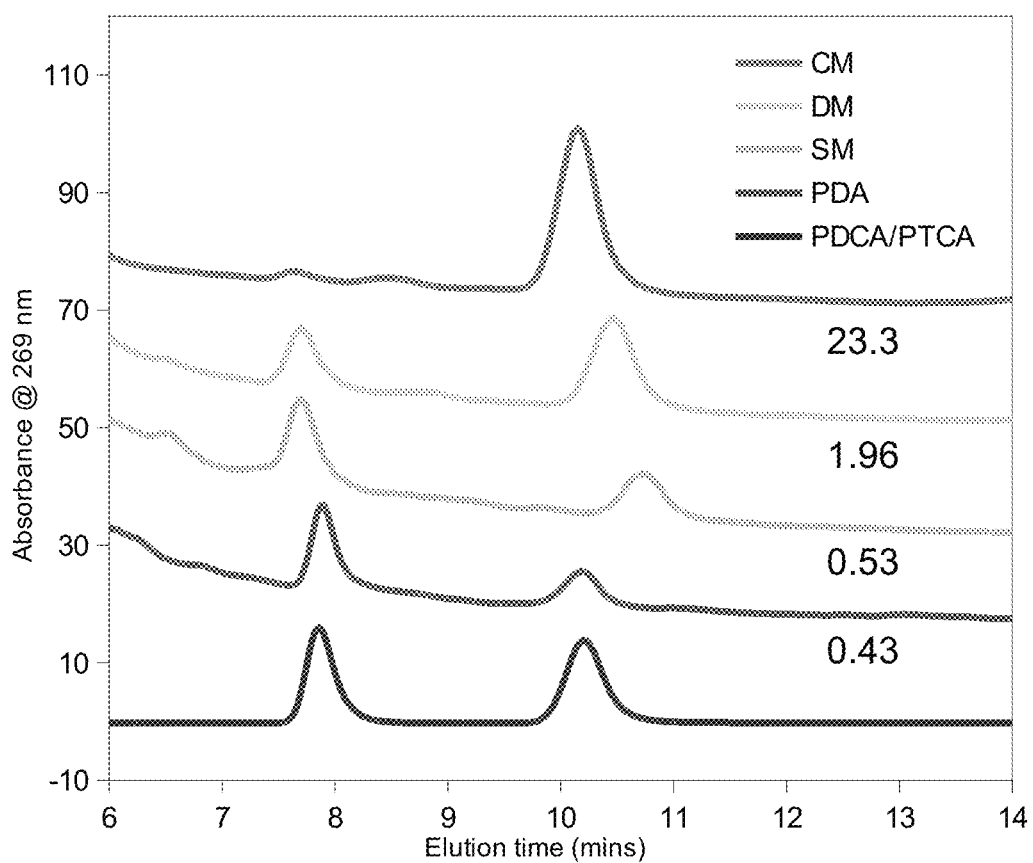
FIG. 15. HPLC analysis with detection at 269 nm of melanin samples after alkaline peroxide degradation assay. The standard shown contained 1 μg/mL of PDCA eluting at 7.9 mins and 1 μg/mL of PTCA eluting at 10.2 mins. The PTCA/PDCA ratios of each sample are labeled below its spectrum.

We hypothesized that the Na cations were shielding the negatively charged carboxyls of DHICA during formation, reducing electrostatic repulsion hence allowing increased polymerization leading to larger DM particle with increased DHICA incorporation. To investigate this, an alkaline peroxide degradation assay was employed to break down the PDA and DM into PTCA and PDCA, the degraded products of DHICA and DHI respectively. As shown in FIG. 15, these products were then quantified using RP-HPLC, giving us a PTCA/PDCA ratio which can indicate the ratio of DHICA/DHI.(27) For comparison, we also performed the assay on PDA, and two commercially available forms of melanin, synthetic melanin (SM) which was prepared by peroxide oxidation of tyrosine, and cuttlefish melanin (CM) which was isolated from *Sepia officinalis*.

The PTCA/PDCA ratio of PDA was the lowest at 0.426±0.02, which is expected as DHICA does not form in PDA. However, there were still measurable levels of PTCA from PDA, which is likely due to DHI subunits that were conjugated to its neighbor via the 2 position.(23) In contrast, DM synthesized using 500 mM NaCl buffer had a PTCA/PDCA ratio of 1.96±0.19, which was significantly higher than that of PDA. This result is in agreement with our previous finding that in contrast to PDA, DM contained carboxylic acids as determined by FTIR (see Example 1). The PTCA/PDCA ratio of DM is also significantly higher than that of SM at 0.533±0.01, which indicates that the method of melanin formation using NaCl alkaline buffer results in higher DHICA content compared to peroxide oxidation of tyrosine, the method that was used to form the commercial SM. Our assay also showed that CM had a much higher ratio of 23.3±0.9, which is consistent with values found in literature.(28) This was not surprising as natural melanins are known to contain about 50% DHICA due to the enzymatic action of dopachrome tautomerase which rearranges dopachrome into DHICA, while synthetic melanins formed without the enzyme only contain about 10% DHICA due to the spontaneous decarboxylation of dopachrome.(29)

Increasing DHICA Content of Melanins.

Figure 16:
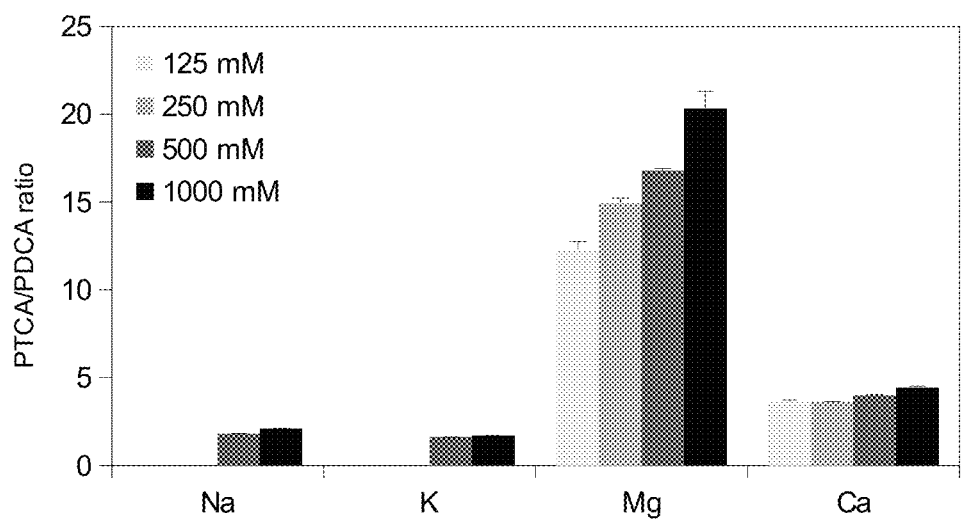
FIG. 16. Effect of type and concentration of salts on DM formation. (A) PTCA/PDCA ratios and (B) Pb(II) binding from 1 mM solution at pH 4.8.
Figure 16:
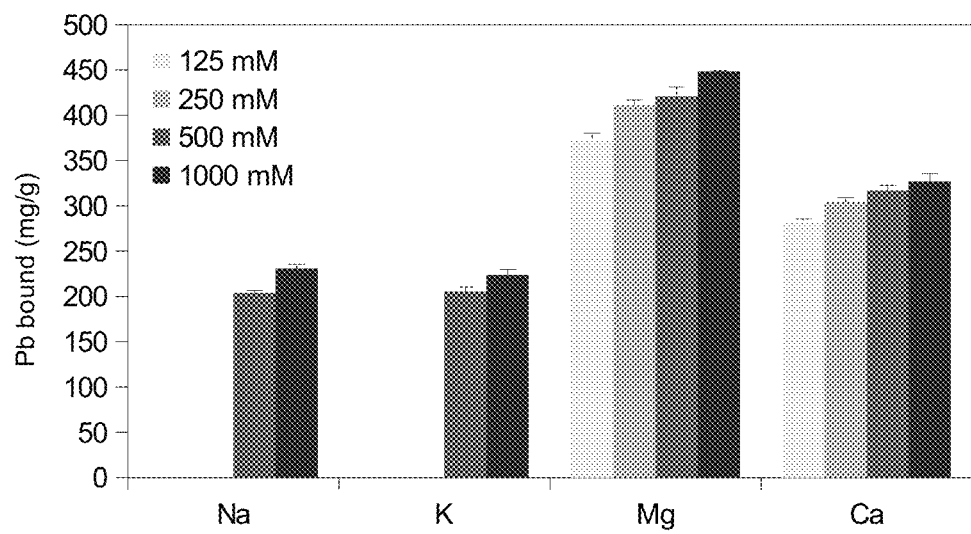

In order to increase the DHICA content of our synthetic melanins, we explored the use of different monovalent and divalent salts at various concentrations in the pH 8.5 buffer during DM formation, namely the chlorides of Na, K, Mg and Ca. For each salt, 125, 250, 500 and 1000 mM was used to form DM to determine the effect of both the type and concentration on the PTCA/PDCA ratio. We observed that while at least 500 mM of NaCl or KCl was required to form insoluble DM without acidification, only 125 mM of $MgCl_2$ or $CaCl_2$ was needed to do the same. As shown in FIG. 16A, using the alkaline peroxide degradation assay, we found a trend of increasing PTCA/PDCA ratio of the DM formed when a higher concentration of the salt was present in the buffer. The use of divalent salts resulted in a significantly higher PTCA/PDCA ratio for DM than when the monovalent salts were used. This suggests that the ionic strength of the buffer during formation of DM plays an important role in influencing the DHICA/DHI ratio of the DM formed. When comparing Na to K and Mg to Ca, the use of the metal with the smaller ionic radii resulted in a higher PTCA/PDCA ratio. This could be due to the metal ions with higher charge density having a stronger effect in charge shielding. The highest PTCA/PDCA ratio achieved in our synthetic melanins was DM formed using 1000 mM $MgCl_2$ which at 20.3 is almost comparable to CM's ratio of 23.3.

We then used the DM formed using the four different salts in a lead binding assay to determine the effect of the salts on the lead binding capacity of the DM formed. In the assay, the samples were mixed with 1 mM of Pb(II) solution for 3 h, centrifuged, and the supernatant analyzed using ICP-MS for changes in Pb concentration. As shown in FIG. 16B, we found that the amount of Pb bound by the DM followed the same order (Mg>Ca>Na~K) as the PTCA/PDCA ratio of the DM, showing that increased DHICA results in increased metal binding.

Heavy Metal Binding.

We continued the metal binding study using DM formed in 20 mM bicine pH 8.5 buffer with either 500 mM NaCl or 500 mM $MgCl_2$, hereon termed DM(Na) and DM(Mg), respectively. Both DM were compared to activated carbon (AC), PDA, SM and CM for binding capacities for lead, copper, cadmium and mercury.

Figure 17:
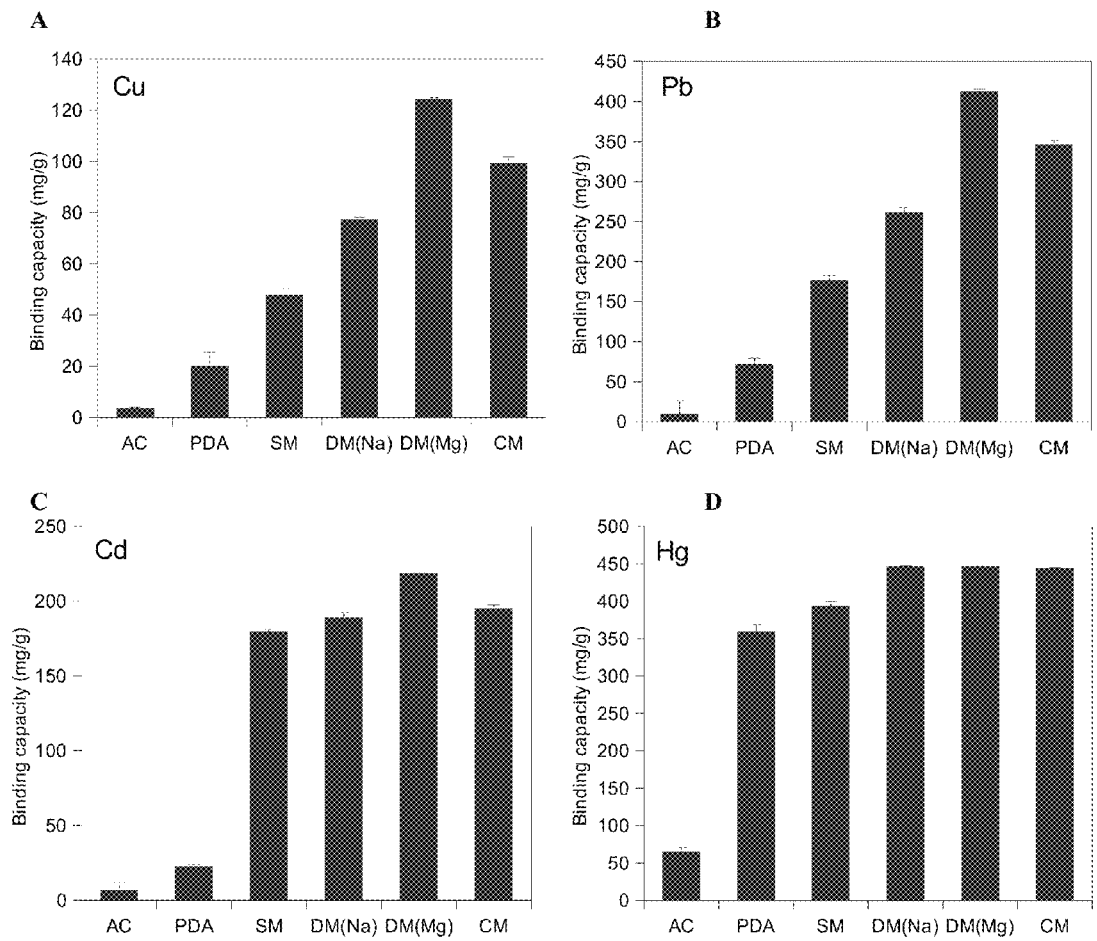
FIG. 17. Binding capacities of AC, PDA, DM(Na) DM(Mg), SM and CM for (A) Cu, (B) Pb, (C) Cd and (D) Hg at 1 mM.

As shown in FIG. 17A, the Cu(II) binding capacity was in the order of DM(Mg)>CM>DM(Na)>SM>PDA. This order matched the order of their PTCA/PDCA ratios, except for DM(Mg) which had a lower PTCA/PDCA ratio but a higher Cu(II) binding capacity than CM. The best performing material was DM(Mg) which bound to 95.6% of available Cu(II), achieving a binding capacity of 124.3 mg/g. CM came in a close second, binding 76.5% of available Cu(II), equating to a binding capacity of 99.5 mg/g. A study by Hong et al. found that fresh sepia melanin bound up to 70 mg/g of Cu(II), close to our own results.(30) In the same study, it was suggested that the Cu(II) binding site in melanin was the catechol group instead of the carboxyl. However, Froncisz & Sarna had earlier used electron paramagnetic resonance spectroscopy to suggest that Cu(II) binds to melanin on the carboxyl when the pH was less than 6.(31, 32) Hong & Simon later concluded that Cu(II) binds first to the catechol site, and then at the carboxyl at higher Cu(II) concentrations.(33) Our results show that melanins with higher DHICA content had increase binding to Cu(II), supporting that the carboxyl groups do participate in Cu(II) binding at pH 4.8.

For Pb(II) binding, PDA bound to about 7 times as much Pb(II) as AC, consistent with previous studies (FIG. 17B).(20) The DHICA-containing melanins all had Pb(II) binding capacities that were significantly higher than that of PDA, in the order of DM(Mg)>CM>DM(Na)>SM. Due to the similar qualitative trend with Cu(II) binding, we speculate that Pb(II) binds similarly to the catechol first, and then to the carboxyl at higher concentrations. It should be noted that DM(Mg) removed over 99% of all the available Pb(II), equating to a binding capacity of 412.4 mg/g.

The trend we observed so far in our results that DM(Mg) could bind more metal ions than CM despite having a lower PTCA/PDCA ratio could be attributed to a combination of factors. Firstly, the CM used are melanin granules consisting of about 5-7% matrix proteins which do not have significant binding to metal ions.(13) The second possible factor could be that residual unoxidized DOPA in DM(Mg) was reducing the metal ions from the solution.

For Cd(II) binding, the DHICA-containing melanins had at least 8 times the binding capacity compared to PDA (FIG. 17C). This large difference could be due to Cd(II) binding more on the carboxyl of DHICA than to the catechol. A study by Chen et al. found that binding of Cd(II) to squid melanin was reduced by competition with macrosalts more so than compared to Pb(II), supporting that electrostatic attraction to the carboxyl was more dominant for Cd(II) binding.(14)

For Hg(II) binding, DM(Na), DM(Mg) and CM performed equally well, removing about 99% of all available Hg(II) (FIG. 17D). PDA and SM removed 80% and 88% of available Hg(II), respectively. The contrast between the Hg(II) binding capacities of PDA and the DHICA-containing melanins was much lower than in the case of the previous 3 metal ions. However, DM(Na), DM(Mg) and CM still removed almost 7 times as much Hg(II) compared to AC. This would suggest that the catechol binding site is a good chelator of Hg(II), more so than the carboxyl.

Pb(II) Binding Affinity and Effect of Contact Time.

Figure 18:
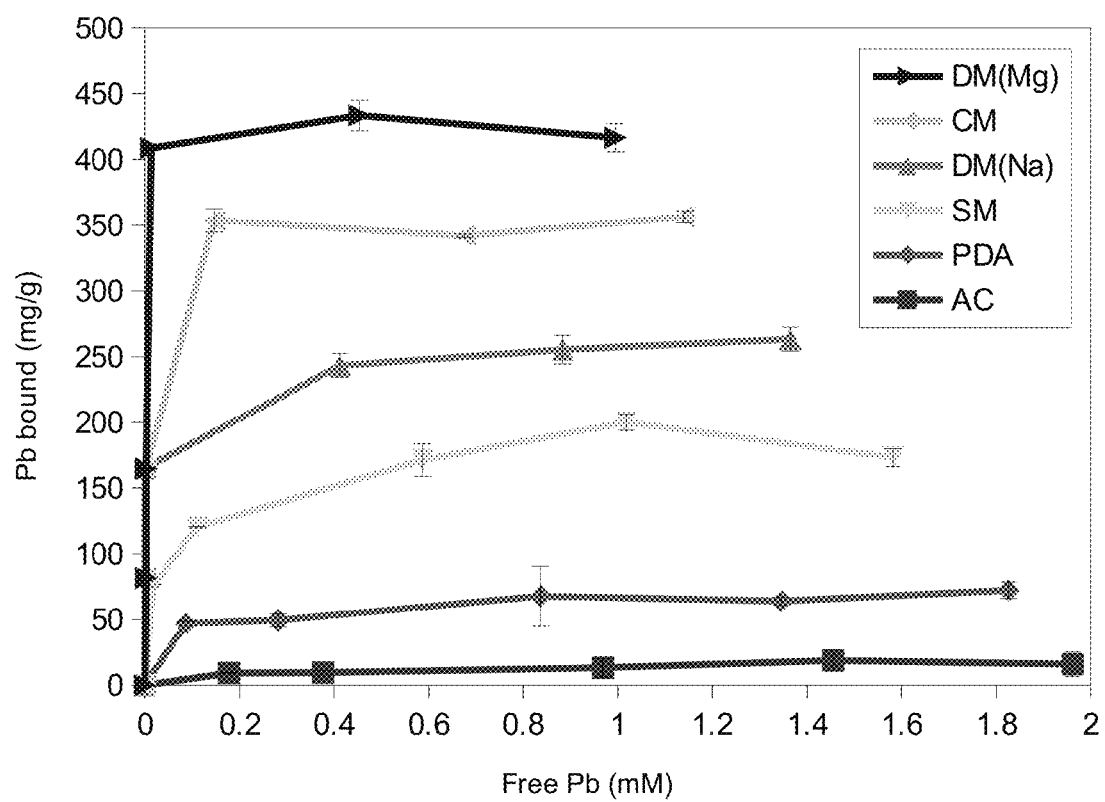
FIG. 18. Pb(II) binding isotherms at pH 4.8.

We further investigated the binding of Pb(II) to our samples at various initial concentrations ranging from 0.2 mM to 2 mM to determine the isotherms (FIG. 18). We note that the binding of metal ions to melanins occur at more than a single type of binding site and has not been shown to be surface adsorption events, and hence do not fit the assumptions of the Langmuir adsorption equation. However, existing literature have used the Langmuir adsorption model to represent an aggregate binding affinities and capacities of metal ions to melanins (34, 35) thus we have done the same for the purpose of making comparisons. As shown in Table 4, both the binding affinities and maximum capacities of our samples followed the same order of DM(Mg)>CM>DM(Na)>SM>PDA>AC. The maximum Pb(II) binding capacity of DM(Mg) is 420.7 mg/g with a binding affinity of 405 mM$^{-1}$. In comparison, AC was found to have a binding capacity of 19.2 mg/g and a binding affinity of 3.5 mM$^{-1}$.

TABLE 4

Langmuir maximum binding capacities, Langmuir affinity constants, and $R^2$ values obtained via linearized Langmuir regression of the Pb(II) binding isotherms.

|  | AC | PDA | SM | DM(Na) | DM(Mg) | CM |
|---|---|---|---|---|---|---|
| $\Gamma_{max}$ (mg/g) | 19.20 | 73.52 | 182.80 | 262.54 | 420.72 | 354.61 |
| K (mM$^{-1}$) | 3.48 | 10.22 | 41.16 | 92.47 | 404.92 | 185.89 |
| $R^2$ | 0.951 | 0.991 | 0.990 | 0.999 | 0.999 | 0.999 |

Demirbas et al. found that a commercially available sulfonated ion exchange resin has a Pb(II) binding capacity of 84 mg/g and a binding affinity of 12.3 mM$^{-1}$.(36) Sono et al. determined that synthetic eumelanin coated onto PVDF via tyrosinase oxidation of DOPA had a Pb(II) binding capacity of 92 mg/g and a binding affinity of 17.4 mM$^{-1}$.(34) The much higher binding capacity and affinity of our DM particles can be attributed to its higher DHICA content due to formation in high ionic strength buffers, though we note that the differences could also be due in part to different methodologies.

Figure 19:
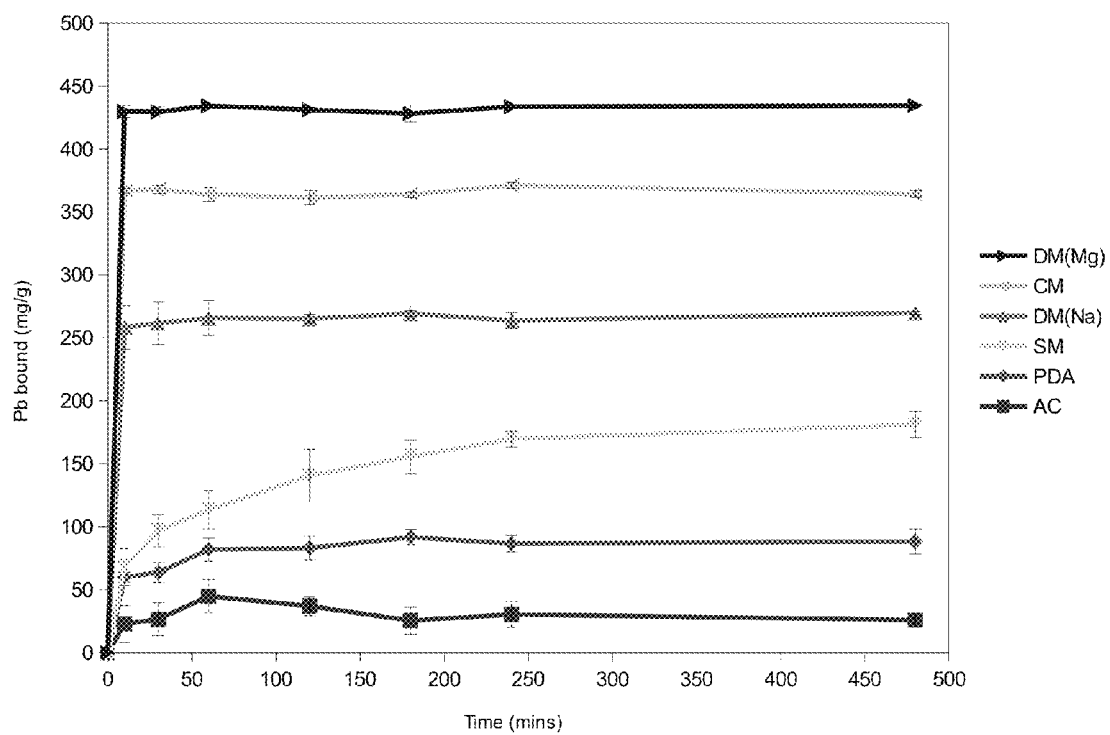
FIG. 19. Effect of contact time on Pb(II) binding from a 1 mM solution.

The dependence of contact time for Pb(II) binding was determined by sampling 1 mM Pb(II) mixed with the melanins at different times. As shown in FIG. 19, we found that DM(Mg), DM(Na) and CM reached their maximum adsorption within 10 mins, which was our first time point. For SM, binding increased until about 240 mins while PDA reached its peak binding at 60 mins. The fast binding of Pb(II) by DM particles makes them suitable as materials for inline water purification.

Surface area. The ability of AC to adsorb heavy metals is attributed to its high surface area. As shown in Table 5, we used Brunauer-Emmett-Teller (BET) surface analysis to determine surface areas of our samples. AC was found to have a surface area of 792.2 m$^2$/g. In comparison, all of the melanins in our study were found to have surface areas below 8 m$^2$/g and can be considered to be non-porous. Both DM(Na) and DM(Mg) have a notably lower surface area than the other melanins, which can be attributed to its larger particle size. Using BET surface area analysis and Barrett-Joyner-Halenda (BJH) pore volume analysis, Liu and Simon also determined that sepia melanin is a non-porous material (37) which is consistent with our finding. Considering the high binding capacities of DM and CM, it is likely that metal binding occurs not only on the surface of the melanin particles, but also throughout the material via the internal diffusion of metal ions. Liu et al. has also hypothesized the existence of ion diffusion channels in sepia melanin.(13)

TABLE 5

BET surface area of AC and various melanins.

| Sample | BET Surface area |
|---|---|
| AC | 792.2 m$^2$/g |
| PDA | 7.70 m$^2$/g |
| SM | 7.66 m$^2$/g |
| DM(Na) | 1.83 m$^2$/g |
| DM(Mg) | 1.44 m$^2$/g |
| CM | 7.23 m$^2$/g |

Yields.

The yields of PDA and DM formation in the 1 gram scale were calculated after three days of lyophilization (dry yield), after equilibrating with atmospheric moisture for one day (eqb. yield). The results, along with the inferred water content, are shown in Table 6.

TABLE 6

Yields of PDA and DM formation and inferred water content.

| Melanin | Dry yield | Eqb. yield | Water content |
|---|---|---|---|
| PDA | 28.95% | 32.95% | 12.14% |
| DM(Na) | 28.14% | 33.93% | 17.07% |
| DM(Mg) | 24.38% | 30.25% | 19.43% |

Conclusion.

In conclusion we have synthesized DM particles with high DHICA content by using alkaline buffers at high ionic strength. We have shown that with increased DHICA content, melanins have higher binding capacities for heavy metals such as Pb(II), Cd(II), Cu(II), and Hg(II). DM particles have been shown to have high binding affinity for Pb(II) and fast binding. Taken together, this study demonstrates that high DHICA synthetic melanins can be promising for use in toxic heavy metal removal. The use of high ionic strength buffers to autoxidize melanins with a DHICA/DHI ratio closer to that of natural eumelanin might also be of interest to researchers using synthetic models of eumelanin.

Example 3

Facile Preparation of DHICA-Enriched DOPA-Melanin for Heavy Metal Capture

In this example, we investigate the formation of insoluble DM particles using high ionic strength buffers, apply them for heavy metal capture, and compare their performance with AC, PDA particles and other forms of melanin. We show that the type and concentration of salt used in the polymerization solution has a significant effect on the ratio of the DHICA to DHI subunits of the DM, which in turn correlates with the ability of the DM to bind heavy metals.

Common methods for removal of high concentrations of heavy metals from water include chemical precipitation, membrane filtration, ion-exchange resins, oxidation-reduction and solvent extraction.[9] However, these methods are often insufficient to reduce heavy metal concentration below strict regulatory requirements.[10] For removal of trace heavy metal ions, adsorbent-based technologies such as activated carbon, chitosan, zeolites and clays have been widely explored.[11] Unfortunately, many of these adsorbents suffer from relatively low binding capacities and weak binding affinities for heavy metal ions.[12] While some progress has been made in attempts to increase both capacity and affinity by chemical modification of existing adsorbents, [12-15] the development of alternative adsorbents is needed.

Figure 27:
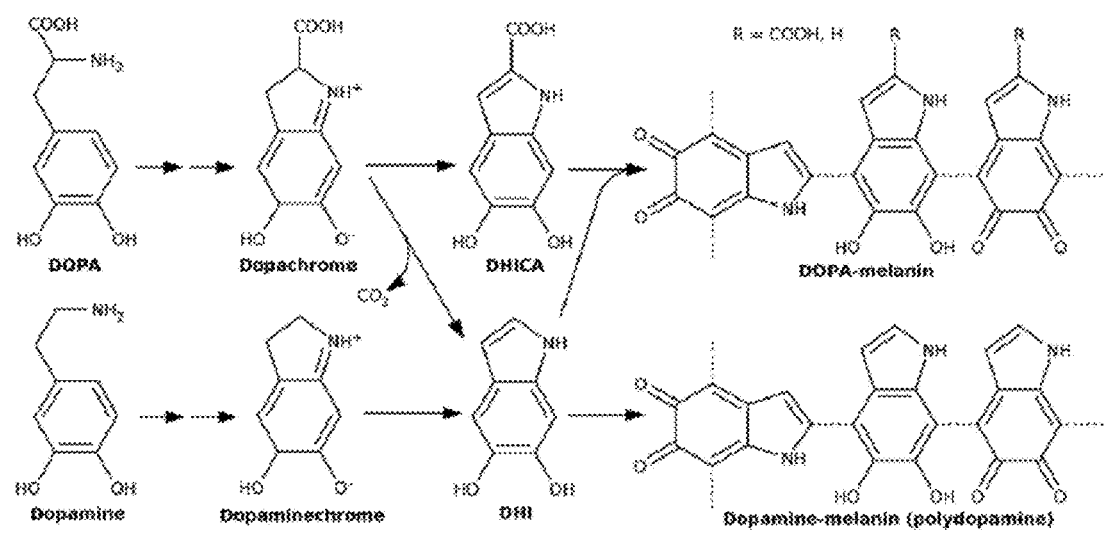
FIG. 27. SCHEME 1

While the exact chemical structure of PDA has yet to be fully elucidated, it is known that it contains mainly DHI,[35] whereas synthetic melanin formed from DOPA would contain both DHI and DHICA subunits (FIG. 27). Since DHICA contains a carboxylic acid which can act as a secondary metal binding site, one would expect synthetic DOPA-melanin (DM) to bind heavy metals with increased capacity and affinity compared to PDA. However, synthetic DM has been shown to contain only about 10% DHICA, compared to 50% found in natural eumelanin.[36] To date, there are few reports of the use of synthetic DM in heavy metal remediation, and we believe this is partly due to the fact that DM formed via autoxidation of DOPA in an alkaline buffer remains soluble above pH 3.[24,37]

In comparison, PDA formed in the same buffer precipitates easily and hence is amenable for physical separation after heavy metal binding.[24] Additionally, autoxidation of DM does not produce coatings as easily as PDA does, especially on negatively charged substrates like metal oxides.[38] Hypothesizing that this is due to the repulsion of the negative charges of the carboxyl of DHICA during formation, limiting polymerization and/or aggregation, we recently showed that the use of high ionic strength buffers afforded the formation of DM films on various substrates, imparting the ability to load and release a cationic drug through electrostatic binding.[39]

Materials and methods. 10,000 ppm standard solutions of Pb(II), Cu(II), Cd(II) and Hg(II) were purchased from Inorganic Ventures (Christiansburg, Va.). Dopamine.HCl, l-DOPA, cuttlefish melanin (CM, catalog number M2649), synthetic melanin (SM, catalog number M8631), and all other chemicals used were purchased from Sigma (St. Louis, Mo.). All H2O used was purified to resistivity ≥18.2 MΩ-cm using a NANOpure Infinity System from Thermolyne Corp. (Dubuque, Iowa). PDCA and PTCA were kindly provided by Dr. Kazumasa Wakamatsu.

Synthesis of Melanins.

PDA was formed by autoxidation of dopamine.HCl (10 mM) in bicine buffer (20 mM, pH 8.5) in an open bottle placed on a rocker for 20 h at room temperature. The solution was then centrifuged at 4500 rcf for 5 mins, the supernatant was decanted, and the pellet was resuspended in H2O. This washing step was repeated 10 times until the supernatant was clear. The pellet was then resuspended in 5 mL of H2O, lyophilized, and stored in a desiccator prior to use. Preparation of DM followed a similar procedure except that l-DOPA (10 mM) was dissolved in bicine buffer (20 mM, pH 8.5) containing 0-1000 mM of either NaCl, KCl, MgCl2, or CaCl2. Washing and isolation of DM was performed as described above.

Alkaline Peroxide Degradation Assay.

Figure 26:
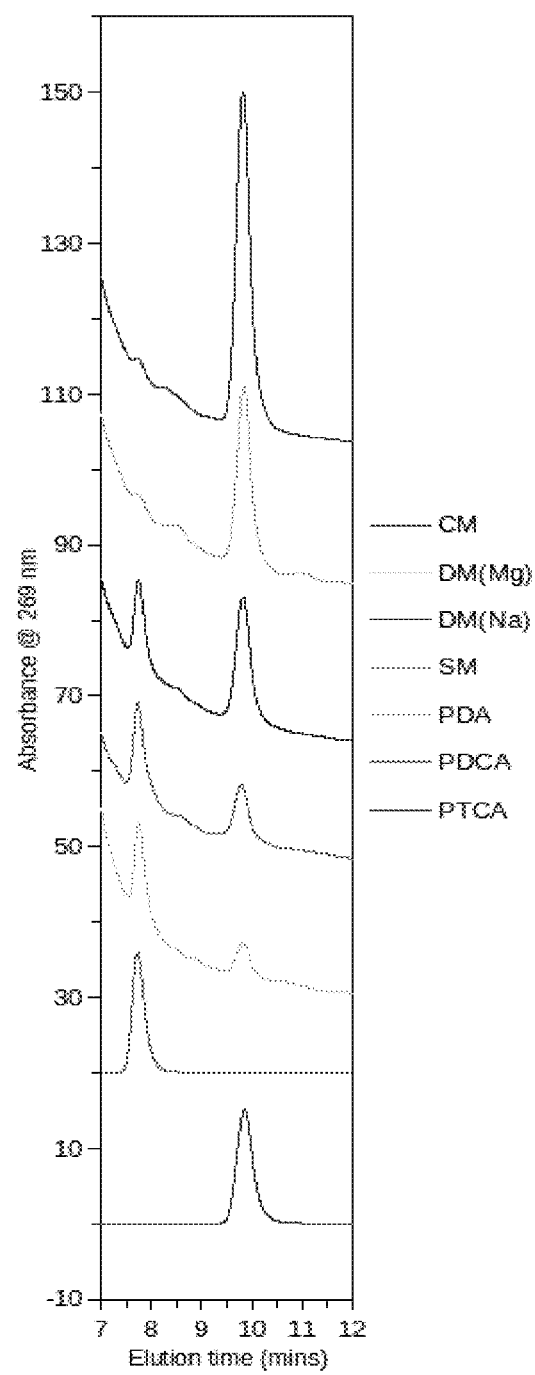
FIG. 26. HPLC analysis with detection at 269 nm of melanin samples after alkaline peroxide degradation assay. Standard solutions of PDCA and PTCA (shown here at 1 μg/mL) eluted at 7.7 mins and 9.8 mins respectively.

DHI and DHICA contents of the natural and synthetic melanins were ascertained using an established protocol[40] with minor modifications. Briefly, 0.1 mg of melanin was suspended in 100 μL of H2O, mixed with 375 μL 1M K2CO2 and 25 μL 30% H2O2, and shaken at room temperature for 20 h. Subsequently, residual H2O2 was decomposed by adding 50 μL 10% Na2SO3, and the mixture was acidified with 140 μL 6M HCl. 80 μL of this mixture were analyzed by RP-HPLC using a C18 column with mobile phase of 0.1 M potassium phosphate buffer (pH 2.1)/methanol, 98:2 (v/v) maintained at 50° C. with flow rate of 0.7 mL/min, and absorbance at 269 nm was monitored. For quantification, standard curves were determined from sampling various concentrations of PDCA and PTCA standard solutions, which were found to elute at 7.7 and 9.8 minutes, respectively, under our conditions (FIG. 26).

Metal Ion Binding.

All metal binding experiments were performed using the batch technique. Metal ion solutions were prepared by dilution of 10,000 ppm stock solutions with H2O to 2 mM (Pb, Cu and Cd) or 4 mM (Hg). The pH was adjusted to 4.8 (Pb, Cu and Cd) or 3.6 (Hg) using NH4OH and HNO3. In a typical experiment, 5 mg of melanin solid was mixed with 10 mL of the metal ion solution in a 15 mL metal-free centrifuge tube. Following 4 h of agitation on a rocker at room temperature, the tubes were centrifuged at 15,000 rcf for 5 mins. The supernatant was then isolated, diluted to within the range of 10-100 ppb metal content, and then analyzed using inductively coupled plasma mass spectrometry (ICP-MS). The amount of metal bound was inferred from the reduction in metal ion concentration of the supernatant using the following equation $$q_e = \frac{(C_0 - C_e)V}{W}$$

where qe is the mass of metal bound per gram of adsorbent, C0 and Ce are the initial and final concentration of metal ion in solution, V is the volume, and W is the mass of adsorbent.

Scanning Electron Microscopy.

PDA and DM particles were suspended in H2O, pipetted onto 1×1 cm silicon wafers and allowed to dry. The samples were then coated with 5 nm osmium and imaged using a Hitachi SU8030 scanning electron microscope at 10 kV.

Optical Microscopy.

DM particles were formed as described above from 5 mM DOPA in pH 8.5 bicine buffer with various concentrations of NaCl. After formation for 16 h, 1 mL of each solution was pipetted into polystyrene 24 well plates and imaged using bright field optical microscopy.

PDA and DM Synthesis.

The solution of dopamine in bicine buffer (20 mM, pH 8.5) darkened over a period of several hours as the PDA formed and began to precipitate. After 16 h, PDA particles were easily collected via centrifugation at 4500 rcf and were resistant to dissolution in H2O. In contrast, DM synthesized from 1-DOPA using this approach remained soluble and could not be isolated by centrifugation. Chio et al. previously made similar observations, and noted that precipitation and isolation of DM required either acidification to pH<3 or addition of salts such as sodium chloride or ammonium sulfate.[37] However, in our attempts, DM formed and isolated using this approach redissolved when suspended in pure H2O.

Figure 20:
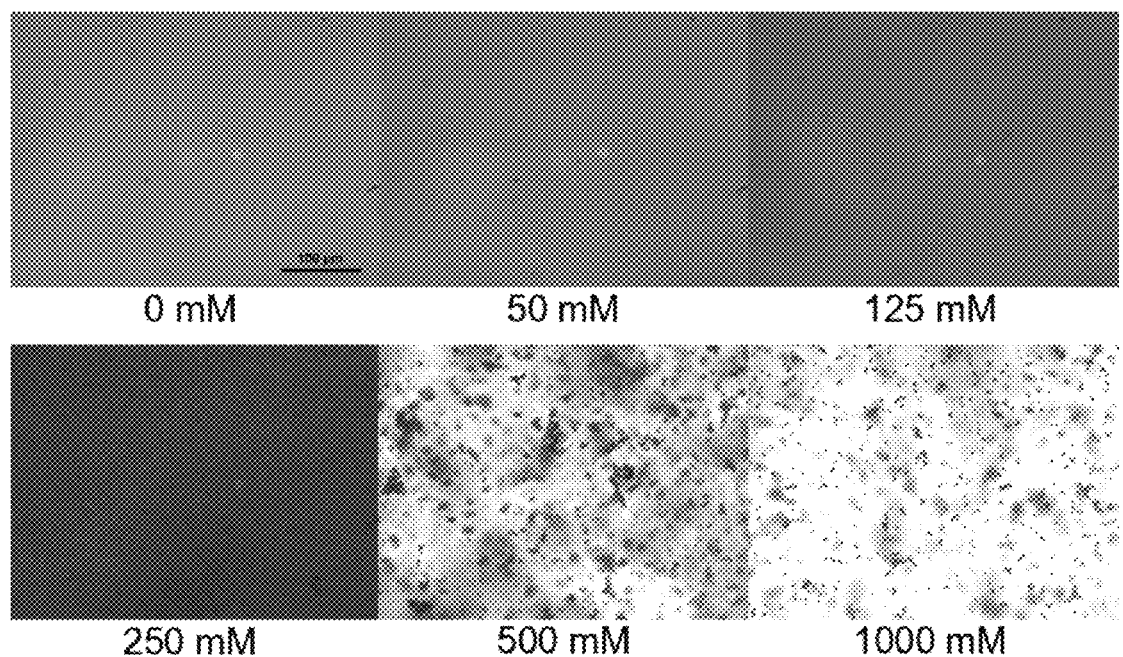
FIG. 20. Seeking an insoluble form of DM that would function well as a solid support for toxic metal removal from water, we allowed DOPA to autoxidize for 16 h in pH 8.5 buffer containing various concentrations of NaCl. The suspensions became darker with increasing salt concentration until 250 mM NaCl, beyond which precipitates were observed by optical microscopy.
Figure 21:
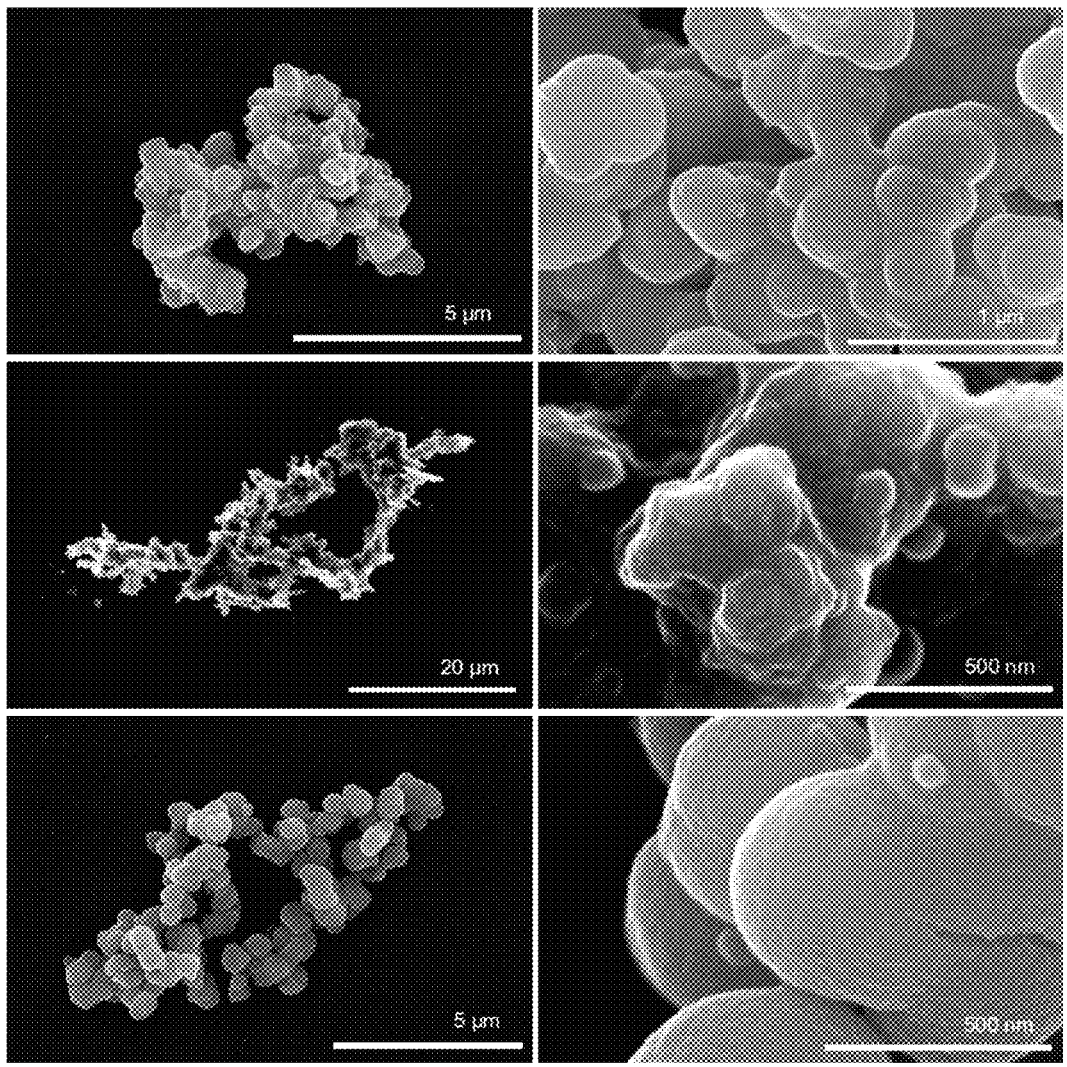
FIG. 21. Scanning electron microscopy revealed the PDA and DM particles to be of variable size and composed of aggregates of smaller sub-micron particles.

Seeking an insoluble form of DM that would function well as a solid support for toxic metal removal from water, we allowed DOPA to autoxidize for 16 h in pH 8.5 buffer containing various concentrations of NaCl. The suspensions became darker with increasing salt concentration until 250 mM NaCl, beyond which precipitates were observed by optical microscopy (FIG. 20). DM solids formed at 500-1000 mM NaCl could be isolated by centrifugation at 4500 rcf and washed in pure H2O without requiring acidification, suggesting that DM formed by autoxidation in the presence of high concentrations of NaCl was physicochemically distinct from that formed at low salt concentration. We hypothesized that the Na+ cations were shielding the negatively charged carboxyls of DHICA during formation, reducing electrostatic repulsion hence allowing increased polymerization leading to larger DM particles. A limited survey of other salts indicated that insoluble DM could also be formed in buffer containing KCl (500 mM), MgCl2 (125 mM) or CaCl2 (125 mM). Scanning electron microscopy revealed the PDA and DM particles to be of variable size and composed of aggregates of smaller sub-micron particles (FIG. 21).

Effect of DM Synthesis Conditions on PTCA/PDCA Ratio.

To determine the DHI and DHICA content of melanin solids, an alkaline peroxide assay was performed, in which the DHICA and DHI subunits of melanin are degraded into pyrrole-2,3,5-tricarboxylic acid (PTCA) and pyrrole-2,3-dicarboxylic acid (PDCA), respectively. PTCA/PDCA ratio is therefore considered a proxy for DHICA/DHI ratio.[41] For comparison, we also performed the assay on PDA, synthetic melanin (SM) which was prepared by peroxide oxidation of tyrosine, and cuttlefish melanin (CM) which was isolated from Sepia officinalis. The assay showed that SM and CM had PTCA/PDCA ratios of 0.63±0.1 and 26.4±1.3 (Table 7), consistent with the literature.[42] The much higher DHICA content of natural melanins is due to the enzymatic action of dopachrome tautomerase (DCT) which rearranges dopachrome into DHICA, whereas synthetic melanin formed without enzyme contains lower DHICA content due to the spontaneous decarboxylation of dopachrome.[36]

TABLE 7

Yields of PDA and DM formation, starting from 1 gram of dopamine. HCl or L-DOPA.

| Melanin | Yield |
| --- | --- |
| PDA | 28.9% |
| DM(Na) | 28.1% |
| DM(Mg) | 24.4% |

The PTCA/PDCA ratio of PDA was the lowest at 0.48±0.03, which is expected as the dopamine precursor lacks a carboxylic acid. Nevertheless, low but measurable levels of PTCA were detected in PDA, which was likely due to DHI subunits that were conjugated via the 2 position.[35] Interestingly, the simple modification of synthesizing DM in 500 mM NaCl buffer increased the PTCA/PDCA ratio to 1.80±0.02, which was significantly higher than that of PDA and SM (p<0.001). This result is in agreement with our previous finding that DM coatings formed at high ionic strength contained carboxylic acids as determined by FTIR.[39] The high PTCA/PDCA ratio of DM indicates that the method of DM autoxidation in alkaline buffered saline results in higher DHICA content compared to peroxide oxidation of tyrosine, the method that was used to form commercial SM.

Figure 22:
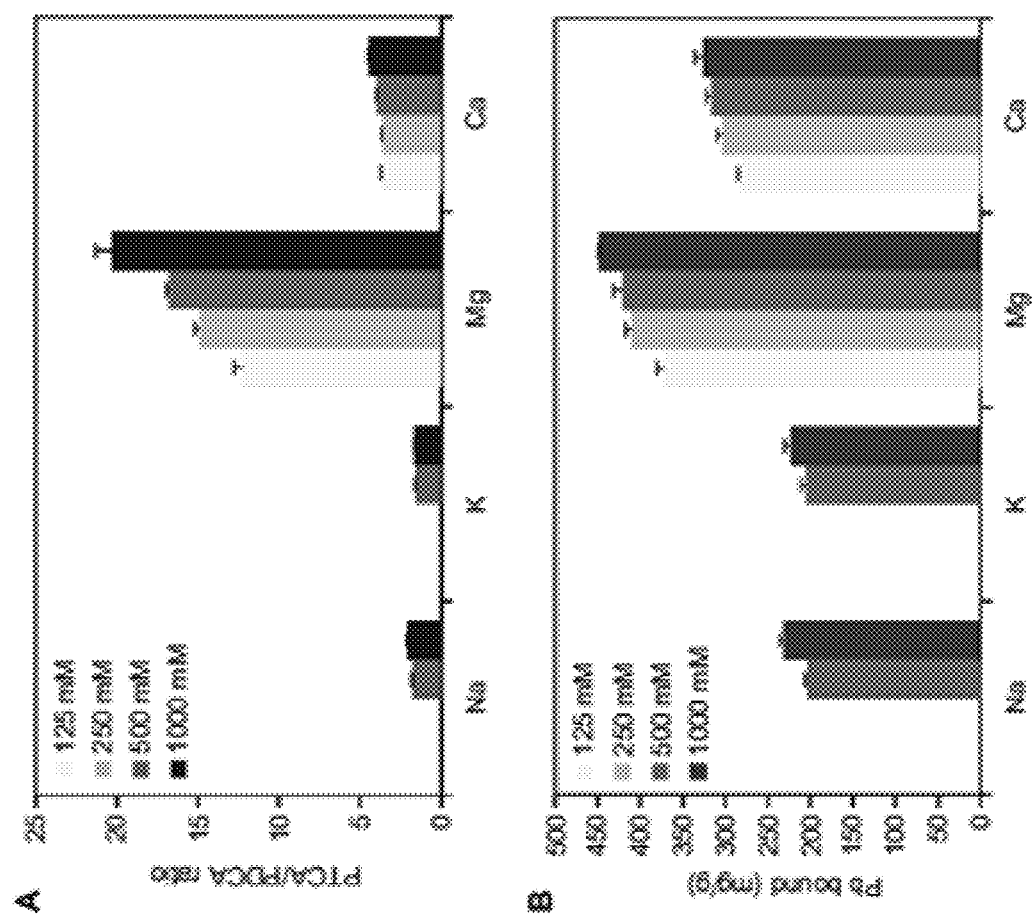
FIG. 22. Chemical structure. (A) While the exact chemical structure of PDA has yet to be fully elucidated, it is known that it contains mainly DHI,[35] whereas synthetic melanin formed from DOPA would contain both DHI and DHICA subunits. We further explored the effect of different concentrations of monovalent (NaCl, KCl) and divalent salts (MgCl2, CaCl2) on PTCA/PDCA ratio and consequently Pb binding. DM was formed in the presence of 125, 250, 500 and 1000 mM of each salt to determine the effect on PTCA/PDCA ratio. For each salt, we found a clear trend ($p<0.01$) of increasing PTCA/PDCA ratio with increasing salt concentration. (B) Here we show that we found that DM formed using MgCl2 bound the most Pb(II), followed by CaCl2. DM formed using NaCl and KCl bound to the least Pb(II). For each type of salt, the amount of Pb(II) bound was also increased with higher concentrations of the salt used during DM formation. This trend correlates to the PTCA/PDCA ratios (Mg>Ca>Na~K) of the DM and suggests that both the type of salt and its concentration can indirectly enhance the amount of Pb(II) binding of DM by increasing its DHICA content during formation.

We further explored the effect of different concentrations of monovalent (NaCl, KCl) and divalent salts (MgCl2, CaCl2) on PTCA/PDCA ratio and consequently Pb binding. DM was formed in the presence of 125, 250, 500 and 1000 mM of each salt to determine the effect on PTCA/PDCA ratio. For each salt, we found a clear trend (p<0.01) of increasing PTCA/PDCA ratio with increasing salt concentration (FIG. 22A). The PTCA/PDCA ratios for NaCl and KCl were similar, with values between 1.6 and 2.1. The use of divalent salts resulted in a significantly higher PTCA/PDCA ratio than monovalent salts during DM formation. Aside from the higher ionic strength provided by the divalent cations, this result might also be related to an increase in catecholate oxidation resulting from additional deprotonation of the catechol during complexation with alkaline-earth metal cations.[43] The highest PTCA/PDCA ratio was 20.3 for DM formed using 1000 mM MgCl2, which was nearly comparable to natural CM (26.4). These data indicate that both the concentration and charge of the salt used in the buffer during DM formation has a strong effect on the DHICA/DHI content.

Pb(II) Binding.

To determine the effect of salt during DM synthesis on its metal binding properties, melanin powders were mixed with 1 mM Pb(II) solution for 3 h, centrifuged, and the supernatant analyzed using ICP-MS for residual Pb(II) concentration. As shown in FIG. 22B, we found that DM formed using MgCl2 bound the most Pb(II), followed by CaCl2. DM formed using NaCl and KCl bound to the least Pb(II). For each type of salt, the amount of Pb(II) bound was also increased with higher concentrations of the salt used during DM formation. This trend correlates to the PTCA/PDCA ratios (Mg>Ca>Na~K) of the DM and suggests that both the type of salt and its concentration can indirectly enhance the amount of Pb(II) binding of DM by increasing its DHICA content during formation.

We subsequently compared the Pb(II) binding properties of DM formed in the presence of either 500 mM NaCl or 500 mM MgCl2 (hereafter termed DM(Na) and DM(Mg), respectively), activated carbon (AC), PDA, SM, and CM. Solids were incubated in 0.2 mM to 2 mM Pb(II) for 4 hours and the unbound Pb(II) determined by ICP-MS. The Langmuir adsorption equation was used to fit the data, although we note that the binding of metal ions to melanins may occur at more than a single type of binding site. Nevertheless, existing literature have used the Langmuir adsorption model to represent aggregate binding capacities and affinities of metal ions to melanins,[44,45] thus we have done the same for the purpose of making comparisons.

Figure 23:
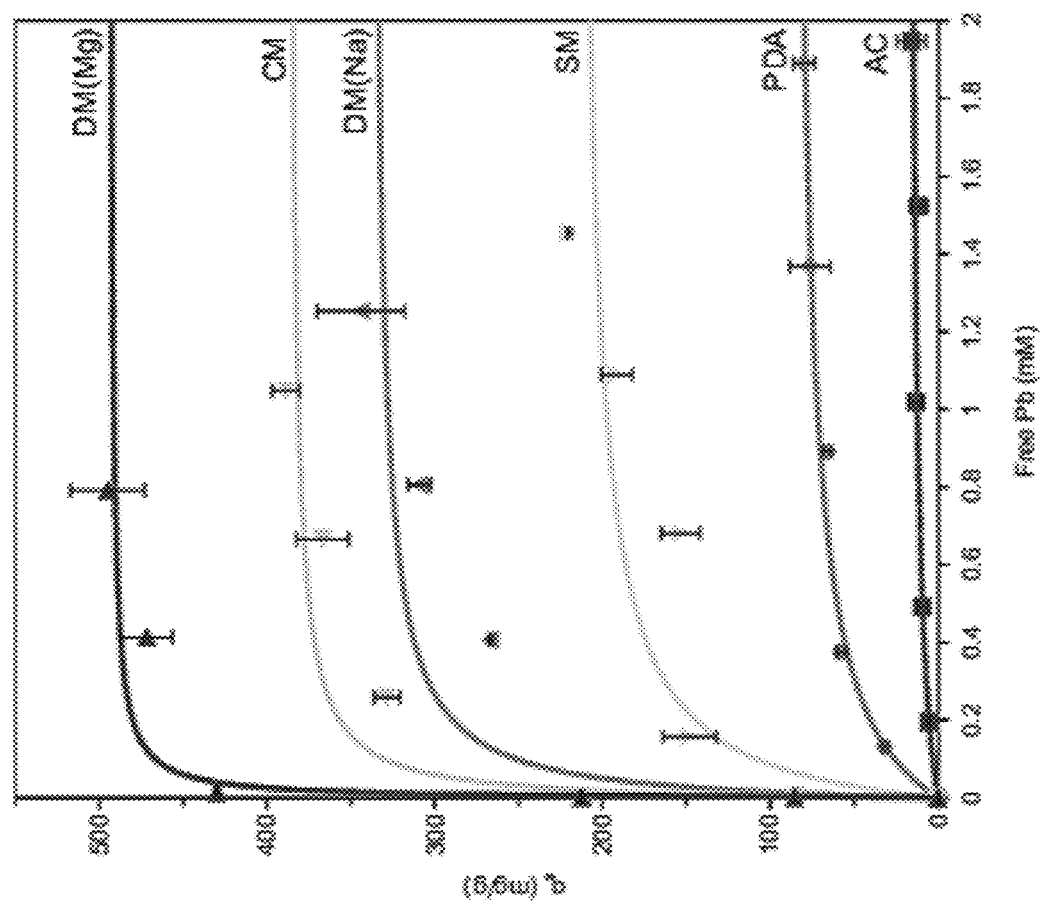
FIG. 23. PDA was found to have a maximum Pb(II) binding capacity of 89.2 mg/g, about 5 times as much as that of AC which was found to be 18.2 mg/g. All the DHICA-containing melanins had maximum Pb(II) binding capacities that were significantly higher than that of PDA, in the order of PDA<SM<DM(Na)<CM<DM(Mg).

As shown in Table 7 and FIG. 23, PDA was found to have a maximum Pb(II) binding capacity of 89.2 mg/g, about 5 times as much as that of AC which was found to be 18.2 mg/g. All the DHICA-containing melanins had maximum Pb(II) binding capacities that were significantly higher than that of PDA, in the order of PDA<SM<DM(Na)<CM<DM(Mg). Similar to the trends seen in FIG. 22, the order of the Pb(II) binding capacities of the melanins followed the same order of their PTCA/PDCA ratios, except for DM(Mg) which had a higher capacity despite having a lower PTCA/PDCA ratio than CM. Remarkably, DM(Mg) had a maximum Pb(II) capacity of 494.1 mg/g and binding affinity of 170.5 mM-1. This binding capacity is higher than that of many other classes of adsorbents (such as zeolites, clays, and chitosan)[11] and even a commercially available sulfonated ion-exchange resin which Demirbas et al. determined to have a Pb(II) binding capacity of 84 mg/g and a binding affinity of 12.3 mM-1.[46]

In recent work, Sono et al. determined that synthetic eumelanin coated onto PVDF via tyrosinase oxidation of DOPA had a maximum Pb(II) binding capacity of 92 mg/g and a binding affinity of 17.4 mM-1.[44] The higher binding capacity and affinity of our DM particles can be attributed to its higher DHICA content resulting from preparation in high ionic strength buffers, though we caution that there were methodological differences between the two studies.

Figure 24:
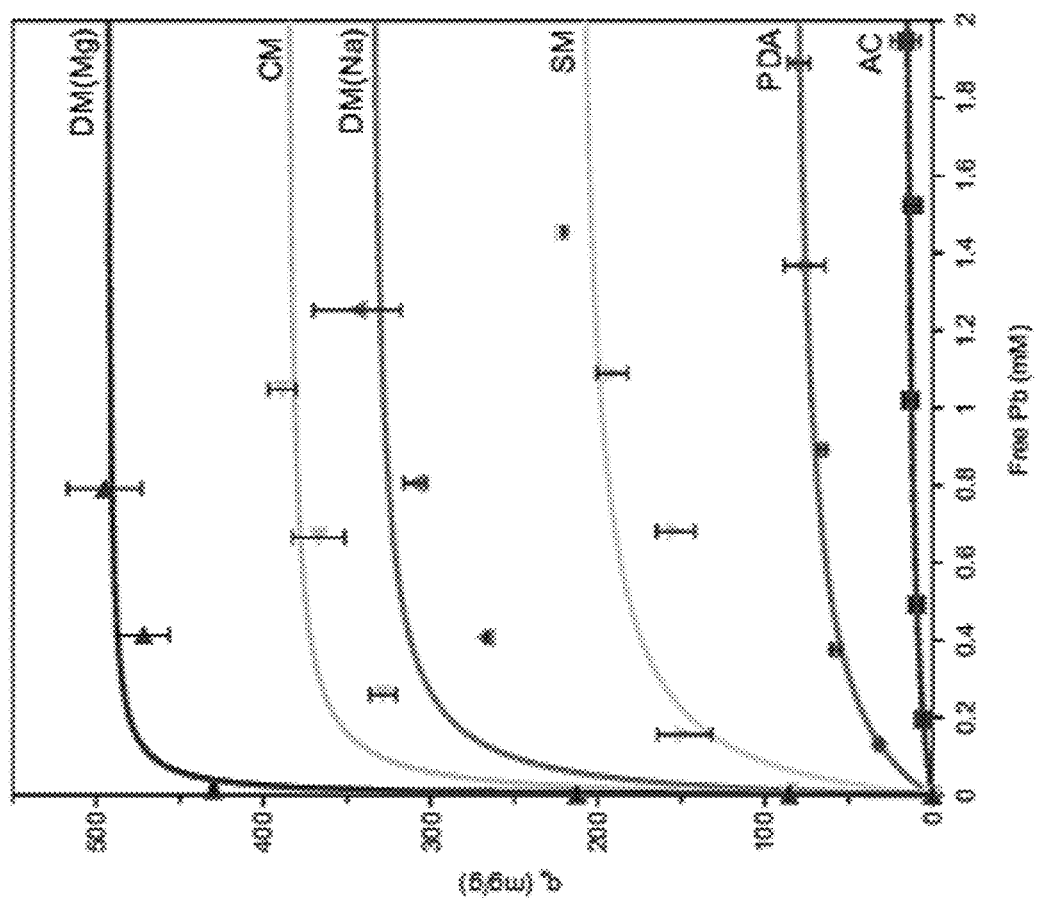
FIG. 24. We found that DM(Mg), DM(Na) and CM reached their maximum adsorption within the first time point studied (15 mins), which was our first time point. For SM and PDA, binding increased until about 60 mins. The fast binding of Pb(II) by DM particles may make them suitable as adsorbents for in-line water purification.

The dependence of contact time for Pb(II) binding was determined by incubating 2 mM Pb(II) with melanin powders over a period of 8 h. As shown in FIG. 24, we found that DM(Mg), DM(Na) and CM reached their maximum adsorption within the first time point studied (15 mins), which was our first time point. For SM and PDA, binding increased until about 60 mins. The fast binding of Pb(II) by DM particles may make them suitable as adsorbents for in-line water purification.

Binding Capacities for Other Heavy Metals.

Figure 25:
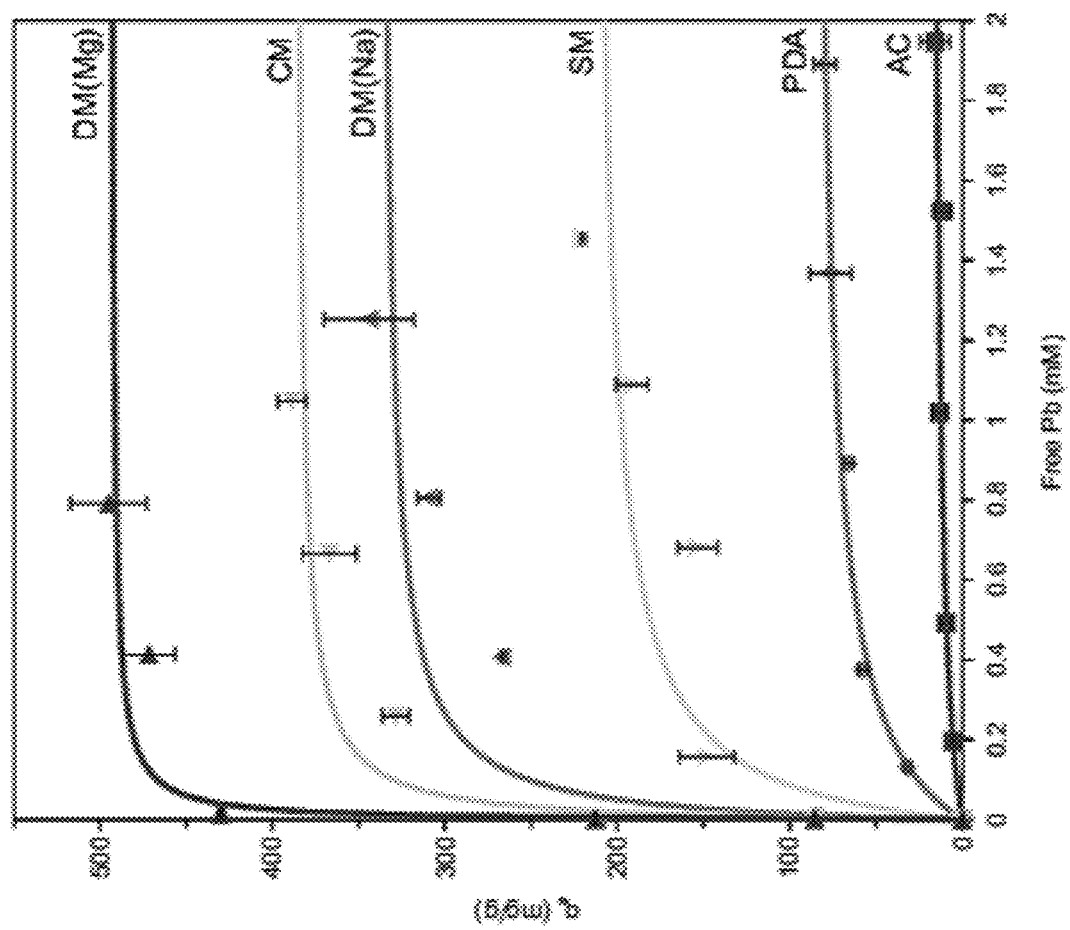
FIG. 25. The Cu(II) binding capacity was in the order of AC<PDA<SM<DM(Na)<CM<DM(Mg). Due to the qualitatively similar binding trend of Pb(II) and Cu(II), we speculate that Pb(II) binds similarly to the catechol of melanins first, and then to the carboxyl at higher concentrations. For Cd(II), we found that melanins rich in DHICA—DM(Na), DM(Mg) and CM, bound 9.6×-13.2× as much as PDA.

Using a similar methodology, the Cu(II), Cd(II) and Hg(II) binding capacities were determined for AC and the various melanins. As shown in FIG. 25A, the Cu(II) binding capacity was in the order of AC<PDA<SM<DM(Na)<CM<DM(Mg). This order was similar to that of Pb(II) binding and matched the order of their respective PTCA/PDCA ratios except for DM(Mg) which, despite its lower PTCA/PDCA ratio, had a higher Cu(II) binding capacity of 148.4 mg/g. We found that CM bound 117.2 mg/g of Cu(II). In comparison, Hong et al. found that fresh sepia melanin bound up to 70 mg/g of Cu(II). The difference could be due to Hong et al. washing the Cu(II) saturated CM granules with 0.1 mM HCl before measuring metal ion concentrations, which might cause some desorption of bound Cu(II).[47]

In the same study, it was suggested that the Cu(II) binding site in melanin was the catechol group instead of the carboxyl. However, Froncisz & Sarna had earlier used electron paramagnetic resonance spectroscopy to suggest that Cu(II) binds to melanin on the carboxyl when the pH was less than 6.[48,49] Hong & Simon later concluded that Cu(II) binds first to the catechol site, and then to the carboxyl at higher Cu(II) concentrations.[50] Due to the qualitatively similar binding trend of Pb(II) (FIG. 25B) and Cu(II), we speculate that Pb(II) binds similarly to the catechol of melanins first, and then to the carboxyl at higher concentrations.

For Cd(II), we found that melanins rich in DHICA—DM(Na), DM(Mg) and CM, bound 9.6×-13.2× as much as PDA (FIG. 25C). This contrast was much larger than in the cases of Pb(II) and Cu(II), which was 4.3×-6.2× and 6.2×-8.8×, respectively. This may suggest that Cd(II) binds predominantly on the carboxyl of DHICA instead of the catechol. A study by Chen et al. found that binding of Cd(II) to squid melanin was reduced by competition with salts more so than when compared to Pb(II), supporting the notion that electrostatic attraction to the carboxyl was more dominant for Cd(II) binding.[21]

For Hg(II), DM(Na), DM(Mg) and CM surprisingly bound between 1128-1244 mg/g of Hg(II) (FIG. 25D). Compared to PDA which bound 622 mg/g of Hg(II), the DHICA rich melanins bound twice as much. This might not be surprising given that neuromelanin has been known to have a high affinity for Hg(II) ions.[22] It is possible that for Hg(II) binding in melanin, the catechol binding site is at least as important as the carboxyl site. Additionally, Hg(II) could be reduced to Hg(0) by a redox reaction with catechol.

For all four heavy metal ions, we observed that DM(Mg) bound more than CM despite having a lower PTCA/PDCA ratio. This can be attributed to a combination of factors. Firstly, the CM used are melanin granules consisting of about 5-7% matrix proteins which are not expected to exhibit significant binding to metal ions.[51] A second factor could be that the CM already contained a small amount of endogenous metal ions that were found in sea water, reducing the apparent binding capacity.[20]

Surface Area.

Brunauer-Emmett-Teller (BET) surface analysis was employed to determine surface areas of our adsorbents (Table 7). AC was found to have a surface area of 792.2 m2/g, whereas all of the melanins in our study were found to have surface areas below 8 m2/g and can be considered essentially non-porous. Both DM(Na) and DM(Mg) have a notably lower surface area than the other melanins, which might be related to its formation at high ionic strength. Using BET surface area analysis and Barrett-Joyner-Halenda (BJH) pore volume analysis, Liu and Simon also determined that CM is a non-porous material[52] which is consistent with our findings. The ability of AC to adsorb heavy metals is attributed to its high surface area. However, considering the high binding capacities yet low surface areas of DM and CM, it is likely that metal binding occurs not only on the surface of the melanin particles, but also throughout the material via the internal diffusion of metal ions. This hypothesis is also supported by Liu et al. who suggested the existence of ion diffusion channels in sepia melanin based on its high binding capacity for Fe(III).[20]

In conclusion, we have synthesized insoluble DM particles by autoxidation in alkaline buffer at high ionic strength. The use of divalent salts and high salt concentrations resulted in higher DHICA content in the DM. In particular, DM formed in MgCl2 buffer had the highest DHICA content, almost matching that of natural melanin. The increased DHICA content in DM was correlated with increased binding of Pb(II). Langmuir maximum binding capacities and binding affinities for Pb(II) were compared across AC, PDA, SM, DM(Na), DM(Mg) and CM and it was found that DM(Mg) had both the highest capacity and affinity. The binding capacities for Cd(II), Cu(II) and Hg(II) were also determined, and similarly, DM(Mg) was found to have significantly higher binding capacities than AC, PDA, SM, DM(Na) and CM. Taken together, this study demonstrates that DHICA-rich synthetic melanins can be easily synthesized at high ionic strength and serve as excellent adsorbents for heavy metal sequestration from aqueous solutions. Synthetic DM formed at high ionic strength might also be of interest to researchers as synthetic models of eumelanin since their DHICA content closely mimics that of natural eumelanin.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

We claim:

1. A method of synthesizing a DOPA-melanin (DM) polymer, the method comprising contacting a reactant having the following formula with a high concentration aqueous salt solution under oxidative conditions:

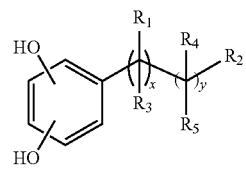

wherein each of $R_1$, $R_3$, $R_4$, and $R_5$ is independently selected from the group consisting of a $C_{1-3}$ alkyl, a primary amine, a secondary amine, a halide, a hydrogen, a hydroxyl, a carboxylic acid, an aldehyde, a carboxylic ester and a carboxamide; wherein at least one of $R_1$, $R_3$, $R_4$, and $R_5$ is a primary or secondary amine; wherein x ranges from 0 to 3 and wherein y ranges from 0 to 3, provided that x or y is at least 1; and wherein $R_2$ is a carboxylic acid;

whereby the DOPA-melanin (DM) polymer is formed.

2. The method of claim 1, wherein x and y are each 1, $R_2$ is —COOH, and $R_5$ is —$NH_2$.

3. The method of claim 2, wherein the reactant is 3,4-dihydroxyphenylalanine (DOPA).

4. The method of claim 1, wherein the concentration of salt in the aqueous salt solution is greater than 100 mM.

5. The method of claim 4, wherein the concentration of salt in the aqueous salt solution is greater than 200 mM.

6. The method of claim 5, wherein the concentration of salt in the aqueous salt solution is greater than 500 mM.

7. The method of claim 1, wherein the salt in the aqueous salt solution is selected from the group consisting of a sodium salt, a potassium salt, a magnesium salt, and a calcium salt.

8. The method of claim 1, wherein the aqueous salt solution is an alkaline solution.

9. The method of claim 1, further comprising the step of contacting the reactant and the high concentration aqueous salt solution with a surface, whereby a DM coating forms on the surface.

10. The method of claim 9, whereby the coating forms on the surface spontaneously.

11. The method of claim 9, wherein the DM coating is greater than 10 nm in thickness.

12. The method of claim 9, wherein the surface comprises a negatively charged substrate.

13. The method of claim 1, wherein the DM polymer formed is in the form of insoluble particles.

14. A DOPA-melanin (DM) polymer formed by performing the method of claim 1.

15. The DM polymer of claim 14, wherein the DM polymer comprises residual carboxylic acid moieties.

16. The DM polymer of claim 14, wherein the DM polymer is in the form of a coating on a substrate surface.

17. The DM polymer of claim 16, wherein the coating is greater than 10 nm in thickness.

18. The coating of claim 16, wherein the substrate surface is the surface of a biomedical device.

19. The DM polymer of claim 14, further comprising a heavy metal ion or a cationic drug captured on the polymer.

20. The DM polymer of claim 19, wherein the cationic drug is a cationic aminoglycoside.

21. The DM polymer of claim 14, wherein the DM polymer is in the form of insoluble particles.

22. A method of reducing the number of metal ions in a fluid comprising the steps of:

contacting the DOPA-melanin (DM) polymer of claim 14 with a fluid comprising one or more metal ions, whereby the DM polymer binds to at least one of the metal ions, thereby reducing the number of metal ions in the fluid.

23. The method of claim 22, wherein the one or more metal ions are selected from the group consisting of $Pb^{2+}$, $Cd^{2+}$, $Cu^{2+}$, and $Hg^{2+}$.

24. A method of delivering a cationic drug comprising the steps of:

contacting the DOPA-melanin (DM) polymer of claim 14 with one or more cationic drugs, whereby the cationic drug is reversibly bound to the DM polymer; and releasing the cationic drug from the DM polymer.

25. The method of claim 24, wherein the cationic drug is a cationic aminoglycoside.

26. The method of claim 25, wherein the aminoglycoside is selected from the group consisting of gentamicin, kanamycin, amikacin, tobramycin, dibekasin, arbekacin, sisomicin, netilmicin, neomycin, and streptomycin.

27. A kit for synthesizing a DOPA-melanin (DM) polymer, the kit comprising:

a) a reactant having the following formula:

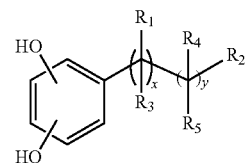

wherein each of $R_1$, $R_3$, $R_4$, and $R_5$ is independently selected from the group consisting of a $C_{1-3}$ alkyl, a primary amine, a secondary amine, a halide, a hydrogen, a hydroxyl, a carboxylic acid, an aldehyde, a carboxylic ester and a carboxamide; wherein at least one of $R_1$, $R_3$, $R_4$, and $R_5$ is a primary or secondary amine; wherein x ranges from 0 to 3 and wherein y ranges from 0 to 3, provided that x or y is at least 1; and wherein $R_2$ is a carboxylic acid;

wherein x ranges from 0 to 10 and wherein y ranges from 0 to 10, provided that x or y is at least 1;

b) a metal salt; and c) instructions for use.

28. The kit of claim 27, wherein the metal salt is selected from the group consisting of a sodium salt, a potassium salt, a magnesium salt, and a calcium salt.

29. The kit of claim 27, further comprising an alkaline buffer.

30. The kit of claim 27 further comprising a substrate surface to be coated with the DM polymer.

31. The kit of claim 30, wherein the substrate surface is the surface of a medical device.

* * * * *